US006921642B2

(12) United States Patent
Kingsmore et al.

(10) Patent No.: US 6,921,642 B2
(45) Date of Patent: *Jul. 26, 2005

(54) PROTEIN EXPRESSION PROFILING

(75) Inventors: Stephen Kingsmore, Guilford, CT (US); Girish Nallur, Guilford, CT (US); Barry Schweitzer, Woodbridge, CT (US)

(73) Assignee: QLAGEN GmbH (DE)

( * ) Notice: Subject to any disclaimer, the term of this patent is extended or adjusted under 35 U.S.C. 154(b) by 221 days.

This patent is subject to a terminal disclaimer.

(21) Appl. No.: 10/341,287

(22) Filed: Jan. 13, 2003

(65) Prior Publication Data

US 2003/0143613 A1 Jul. 31, 2003

Related U.S. Application Data

(63) Continuation of application No. 09/597,836, filed on Jun. 20, 2000, now Pat. No. 6,531,283.

(51) Int. Cl.[7] ............................ C12Q 1/68; C12P 19/34; C12M 1/00; C07H 21/04; C07K 1/00
(52) U.S. Cl. ........................ 435/6; 435/91.1; 435/91.2; 435/283.1; 536/23.1; 536/24.3; 536/24.32; 536/24.33; 530/350
(58) Field of Search .......................... 435/6, 7.92, 91.2, 435/91.1, 283.1; 536/24.3, 24.32, 24.33, 23.1; 530/350

(56) References Cited

U.S. PATENT DOCUMENTS

| | | | |
|---|---|---|---|
| 5,001,050 A | 3/1991 | Blanco et al. | |
| 5,198,543 A | 3/1993 | Blanco et al. | |
| 5,443,986 A | 8/1995 | Haughland et al. | |
| 5,648,245 A | 7/1997 | Fire et al. | |
| 5,854,033 A | 12/1998 | Lizardi | |
| 5,854,053 A | 12/1998 | Donovan et al. | |
| 5,866,336 A | 2/1999 | Nazarenko et al. | |
| 5,876,924 A | 3/1999 | Zhang et al. | |
| 5,942,391 A | 8/1999 | Zhang et al. | |
| 6,033,881 A | 3/2000 | Himmler et al. | |
| 6,096,880 A | 8/2000 | Kool | |
| 6,117,635 A | 9/2000 | Nazarenko et al. | |
| 6,143,495 A | 11/2000 | Lizardi et al. | |
| 6,183,960 B1 | 2/2001 | Lizardi | |
| 6,203,984 B1 | 3/2001 | Hu et al. | |
| 6,210,884 B1 | 4/2001 | Lizardi | |
| 6,221,603 B1 | 4/2001 | Mahtani et al. | |
| 6,255,082 B1 | 7/2001 | Lizardi | |
| 6,291,187 B1 | 9/2001 | Kingsmore et al. | |
| 6,323,009 B1 | 11/2001 | Lasken et al. | |
| 6,329,150 B1 | 12/2001 | Lizardi et al. | |
| 6,344,329 B1 | 2/2002 | Lizardi | |
| 6,531,283 B1 * | 3/2003 | Kingsmore et al. | 435/6 |

FOREIGN PATENT DOCUMENTS

| | | |
|---|---|---|
| EP | 0 745 690 A2 | 12/1996 |
| WO | WO 97/19193 | 5/1997 |
| WO | WO 99/31276 | 6/1999 |
| WO | WO 00/71562 A1 | 11/2000 |

OTHER PUBLICATIONS

Schweitzer et al. Immunoassays with rolling Circle DNA amplification: A versatile platform for ultrasensitive antigen detection. PNAS, vol. 97, No. 18, pp. 10113–10119, Aug. 2000.*

Ekins, Roger. Ligand Assays: from electrophoresis to miniaturized microarrays. Clinical Chemistry, vol. 44, No. 9, pp. 2015–2030, 1998.*

Loakes et al. "5–Nitroindole as a universal base analogue" Nucleic Acids Res. 1994, 22(20):45039–4043.

Baner et al. Signal Amplification of Padlock Probes by Rolling Circle Replication, *Nucleic Acids Research, Oxford University Press, Surrey*, 26(22):5073–5078 (1998), XP002112357.

Gusev et al. Rolling Circle Amplification: A New Approach to Increase Sensitivity for Immunohistochemistry and Flow Cytometry, *American Journal of Pathology*, 159(1):63–69 (Jul. 2001).

Lizardi et al. Mutation Detection and Single–Molecule Counting Using Isothermal Rolling–Circle Amplification, *Nature Genetics*, 19:225–232 (1998).

(Continued)

*Primary Examiner*—Kenneth R. Horlick
*Assistant Examiner*—Cynthia Wilder
(74) *Attorney, Agent, or Firm*—Needle & Rosenberg, P.C.

(57) ABSTRACT

Disclosed are compositions and methods for detecting small quantities of analytes such as proteins and peptides. The method involves associating a primer with an analyte and subsequently using the primer to mediate rolling circle replication of a circular DNA molecule. Amplification of the DNA circle is dependent on the presence of the primer. Thus, the disclosed method produces an amplified signal, via rolling circle amplification, from any analyte of interest. The amplified DNA remains associated with the analyte, via the primer, and so allows spatial detection of the analyte. The disclosed method can be used to detect and analyze proteins and peptides. Multiple proteins can be analyzed using microarrays to which the various proteins are immobilized. A rolling circle replication primer is then associated with the various proteins using a conjugate of the primer and a molecule that specifically binds the proteins to be detectable. Rolling circle replication from the primers results in production of a large amount of DNA at the sites in the array where the proteins are immobilized. The amplified DNA serves as a readily detectable signal for the proteins. The disclosed method can also be used to compare the proteins expressed in two or more different samples. The information generated is analogous to the type of information gathered in nucleic acid expression profiles. The disclosed method allows sensitive and accurate detection and quantitation of proteins expressed in any cell or tissue.

36 Claims, 18 Drawing Sheets

OTHER PUBLICATIONS

Mullenix et al. Allergen–specific IgE Detection on Microarrays Using Rolling Circle Amplification: Correlation with in Vitro Assays for Serum IgE, *Clinical Chemistry*, 47(10):1926–1929 (2001).

Nuovo, et al. In Situ Amplification Using Universal Energy Transfer–labeled Primers, *The Journal of Histochemistry & Cytochemistry, The Histochemical Society, Inc., New York, New York* 43(3):273–279 (1999), XP008002684.

Schweitzer et al. Immunoassays with Rolling Circle DNA Amplification: A Versatile Platform for Ultrasensitive Antigen Detection, *PNAS*, 97(18):10113–10119 (Aug. 29, 2000).

Schweitzer et al. Multiplexed Protein Profiling on Microarrays by Rolling–Circle Amplification, *Nature Biotechnology*, 20:359–365 (Apr. 2002).

Tyagia et al. Molecular Beacons: Probes that Fluoresce upon Hybridization, *Nature Biotechnology*, 14:303–308 (Mar. 1996), XP000196024.

Chang "The Pharmacological Basis of Anti–IgE Therapy" *Nature Biotech.* 18:157–162 (2000).

Oda et al. "Accurate Quantitation of Protein Expression and Site–Specific Phosphorylation" *Biotechniques* 28: 944–957 (2000).

Patton "Making Blind Robots See: The Synergy Between Fluorescent Dyes and Imaging devices in Automated Proteomics" *Proc. Natl. Acad. Sci USA* 96: 6591–6596 (1999)et al.

Mendoza et al. "High–Throughput Microarray–Based Enzyme–Linked Immunosorbent Assay (Elisa)" *Electrophoresis* 18: 533–537 et al.

Anderson et al. "A Comparison of selected mRNA and Protein Abundance in Human Liver" *Mol. Cell. Biol.* 19: 1720–1730 (1999).

Patton "Protome Analysis II. Protein Subcellular Redistribution: Linking Physiology to Genomics via the Proteome and Separation Technologies Involved" *DNA Microarrays: A Practical Approach*. (Oxford University Press, New York, 1999) 1–16.

Gygi et al. "Correlation between Protein and mRNA Abundance in Yeast" *J. Chromatogr.* 722: 203–223, (1999).

Lizardi et al. "Mutation detection and Single–Molecule Counting Using Isothermal Rolling–Circle Amplification" A *Nature Genet.* 19: 225–232 (1998).

Ekins "Ligand Assay: From Electrophoresis to Miniaturized Microarrays" *Clin. Chem.* 44: 2015–2030 (1998).

Wang et al. "Large–Scale Indentification, Mapping, and Genotyping of Single–Nucleotide Polymorphisms in the Human" *Science* 280: 1077 (1998).

Brush "DyeHard: Protein Gell Staining Product" *The Scientist* (12(10):16), www.the–scientist.com (May 11, 1998).

Silzel et al. "Mass–sensing, Multianalyte Microarray Immunoassay with Imaging Detection" *Clin. Chem.* 44: 2036–2043 (1998).

Humphrey–Smith et al. "Proteome Analysis: Genomics via the Output Rather Than the Input Code" *J. Protein. Chem.* 16: 537–544 (1997).

Speicher et al. "Karyotyping Human Chromosomes by Combinatorial Multi–flour Fish" *Nature Genet.* 12:368–375 (1996).

Tyagi et al. "Molecular Beacons: Probes that Fluoresce upon Hybridization" *Nature Biotechnology* 14:303–308 (1996).

Patton et al. "Components of the Protein Synthesis and Folding Machinery are Induced in Vascular Smooth Muscle Cells by Hypertrophic and Hyperplastic Agents" *J. Biol. Chem.* 270: 21404–21410 (1995).

Fleischmann et al. "Whole–Genome Random Sequencing and Assembly of Haemophilus Influenzae Rd" *Science* 269: 496 (1995).

Wirth et al. "Staining Methods in Gel Electrophoresis, including the Use of Multiple Detection Methods" *J. Chromatogr* 698: 123–143 (1995).

AAAI Board of Directors "Measurement of Specific and Nonspecific $IgG_4$ Levels as Diagnostic and Prognostic Tests for Clinical Allergy" *J Allergy Clin Immunol.* 95:652–654 (1995).

Hendrickson et al. "High Seneitivity Multianalyte Immunoassay using Covalent DNA–labeled Antibodies and Polymerase Chain Reaction" *Nucleic Acids Res.* 23: 522–529 (1995).

Lesnick et al. "Relative Tehrmodynamic Stability of DNA, RNA, and DNA:RNA Hybrid Duplexes: Relationship with Base Composition and Structure" *Biochemistry* 34:10807–10815 (1995).

Stimpson et al. "Real–time Detection of DNA Hybridization and melting on Oligonucleotide arrays by using Optical Wave Guides" *Proc. Natl. Acad. Sci. USA* 92:6379–6383 (1995).

Kaboord et al. "Accessory Proteins Function as Mathmakers in the assembly of the T4 DNA Polmerase Holoenzyme" *Curr. Biol.* 5:149–157 (1995).

Rigler et al. "Differences in the Mechanism of Stimulation of tT7 DNA Polymerase by Two Binding Modes od *Escherichia coli* Single–stranded DNA–binding Protein" *J. Biol. Chem.* 270:8910–8919 (1995).

Fire et al. "Rolling Replication of short DNA Circles" *Proc. Natl. Acad. Sci. USA* 92:4641–4645 (1995).

Waggoner, "Covalent Labeling of Proteins and nucleic Acids with Fluorophores" *Meth. Enzymology* 246:362–373 (1995).

Skaliter et al. "Rolling circle DNA replication in Vitro by a Complex of Herpes Simplex Virus Type 1–Encoded Enzymes" *Proc. Natl. Acad. Sci. USA* 91(22):10665–10669 (1994).

Fields et al. "How Many Genes in the Human Genome" *Nature Genet.* 7: 345 (1994).

Nielsen et al. "Peptide Nucleic Acid (PNA)—A DNA Mimic with a Peptide Backbone" *Bioconjug. Chem.* 5:3–7 (1994).

Pease et al. "Light–Generated Oligonucleotide Arrays for Rapid DNA Sequence Analysis" *Proc. Natl. Acad. Sci. USA* 91(11):5022–5026 (1994).

Guo et al. "Direct Fluorescence Analysis of Genetic Polymorphisms by Hybridization with Oligonucleotide Arrays on Glass Supports" *Nucleic Acids Res.* 22:5456–5465 (1994).

Zhu et al. "Purification and Characterization of PRD1 DNA Polymerase" *Biochim. Biophys. Acta.* 11219:267–276 (1994).

Yu, "Cyanine Dye dUTP Analogs for Enzymatic Labeling of DNA Probes" *Nucleic Acids Res.* 22:3226–3232 (1994).

Zijderveld et al. "Helix–Destabilizing Properties of the Adenovirus DNA–Binding Protein" *J. Virology* 68(2):1158–1164 (1994).

Boehmer et al. "Herpes Simplex Virus Type 1 ICP8: Helix–Destabilizing Properties" *J. Virology* 67(2):711–715 (1993).

Kong et al. "Characterization of a DNA Polymerase from the *Hyperthermophile archaea Thermococcus litoralis*" *J. Biol. Chem.* 268:1965–1975 (1993).

Hoy et al. "Bromodeoxyuridine/DNA analysis of Replication in CHO Cells after Exposure to UV Light" *Mutation Research* 290:217–230 (1993).

Wansick et al. "Fluorscent Labeling of Nascent RNA Reveals Transcription by RNA Polymerase II in Domains Scattered Throughout the Nucleus" J. *Cell Biology* 122:283–293 (1993).

Tsurumi et al. "Functional Interaction between Epstein–Barr Virus DNA Polymerase Catalytic Subunit and its Accessory Subunit in Vitro" *J. Virology* 67(12):7648–7653 (1993).

Siebel et al. "A novel RNA Helicase from Calf thymus" *J. Biol. Chem.* 267:13629–13635 (1992).

Kerkhof, "A Comparison of Substrates for Quantifying the Signal from a Nonradiolabeled DNA Probe" *Anal. Biochem.* 205:359–364 (1992).

*Protein immobilization: fundamentals and applications*, Richard F. Taylor, ed. (M. Dekker, New York, 1991).

Khrapko et al. "Hybridization of DNA with Oligonucleotides immobilized in gel: A Convenient Method for Detecting Single Base Substitutions" *Mol Biol* (*Mosk*) (*USSR*) 25:718–730 (1991).

Chatterjee et al. "Cloning and Overexpression of the Gene Encoding Bacteriophage T5 DNA polymerase" *Gene* 97:13–19 (1991).

Rychlik et al. "Optimization of the Annealing temperature for DNA Amplication in Vitro" *Nucleic Acids Res.* 18:6409–6412 (1990).

McGraw et al. "Sequence–Dependent Oligonucleotide–Target Duplex Stabilities: rules from Empirical Studies with a Set of Twenty–Mers" *Biotechniques* 8:674–678 (1990).

Matsumoto et al. "Primary Structure if Bacteriophage M2 DNA Polymerase: Conserved within Protein–Priming DNA polymerases and DNA polymerase 1 of *Escherichia coli*" *Gene* 84:247 (1989).

Tabor et al. "Selective Inactivation of the Exonuclease Activity of Bacteriophage T7 DNA Polymerase by In Vitro Mutagenesis" *J. Biol. Chem.* 264:6447–6458 (1989).

Arnold et al. "Assay Formats Involving Acridinium–Ester––Labeled DNA Probes" *Clinical Chemistry* 35:1588–1594 (1989).

Mujumdar et al. "Cyanine Dye Labeling Reagents Containing Isothiocyanate Groups" *Cytometry* 10:11–19 (1989).

Ernst et al. "Cyanine Dye labeling Reagents for Sulfhydryl Groups" *Cytometry* 10:3–10 (1989).

Sambrook et al. *"Molecular Cloning: A Laboratory Manual,"* 2nd Edition (Cold Spring Harbor Laboratory Press, Cold Spring Harbor, N.Y., 1989) Chapters 5, 6).

Johnstone et al. *"Immunochemistry In Practice"* (Blackwell Scientific Publications, Oxford, England, 1987) pp. 209–216 and 241–242.

Jung et al. "Bacteriophage PRD1 DNA Polymerase: Evolution of DNA Polymerases" *Proc. Natl. Acad. Sci. USA* 84:8287 (1987).

Tabor et al. "Selective Oxidation of the Exonuclease Domain of Bacteriophage T7 DNA Polymerase" *J. Biol. Chem.* 262:15330–15333 (1987).

Itakura et al. "Synthesis and Use of Synthetic Oligonucleotides" *Ann. Rev. Biochem.* 53:323–356 (1984).

Langer et al. "Enzymatic Synthesis of Biotin–Labeled Polynucleotides; Novel Nucleic Acid Affinity Probes" *Proc. Natl. Acad. Sci. USA* 78:6633 (1981).

Narang et al. "Chemical Synthesis of Deoxoligonucleotides by the Modified Triester Method" *Methods Enzymol.*, 65:610–620 (1980).

Jacobsen et al. "The N–Terminal Amino–Acid Sequences of DNA Polymerase 1 from *Eescherichis coli* and of the Large and the Small Fragments Obtained by a limited Proteolysis" *Eur. J. Biochem.* 45:623–627 (1974).

M. Schena et al. "DNA Microarrays: A Practical Approach" (Oxford University Press, New York, 1999) 1–16.

* cited by examiner

- Anchor analyte capture agent (protein, antibody or other interactant)
- Incubate with sample containing analyte
- Incubate with reporter binding primer 1 (to detect unmodified) and reporter binding primer 2 (to detect modified, e.g. phosphorylated) proteins.

- Create mRNA-protein fusion library by in vitro translation
- Capture by hybridization on positional DNA array
- Incubate with RCA platform conjugated to ligands that interact with protein
- Perform RCA signal amplification

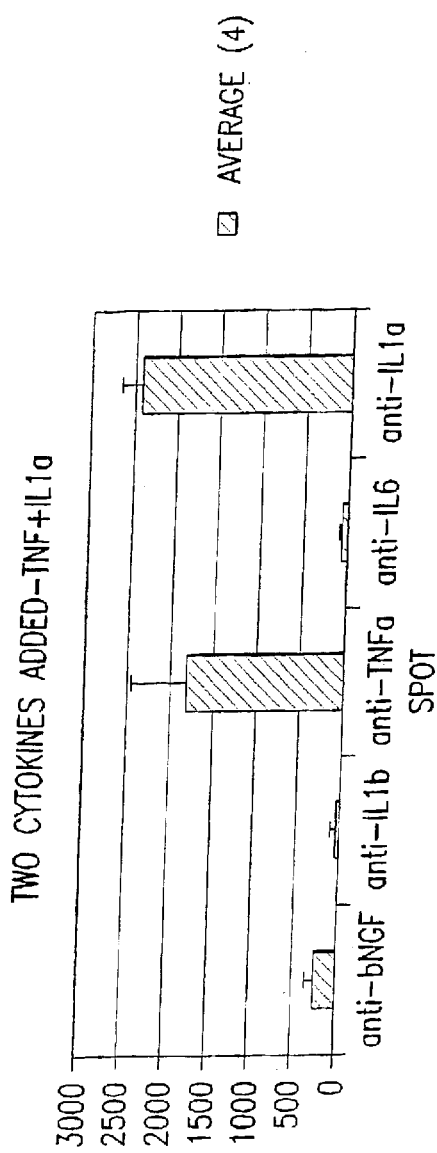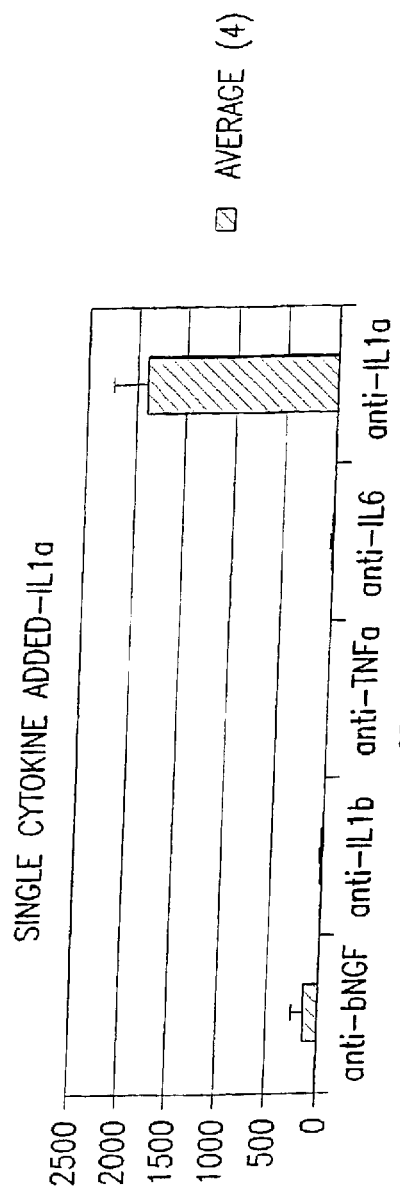

SEQUENCE LISTING

<160> NUMBER OF SEQ ID NOS: 8

<210> SEQ ID NO 1
<211> LENGTH: 40
<212> TYPE: DNA
<213> ORGANISM: Artificial Sequence
<220> FEATURE:
<221> NAME/KEY: misc_feature
<222> LOCATION: (1)
<223> OTHER INFORMATION: Thiol bound at 5' end
<220> FEATURE:
<223> OTHER INFORMATION: Description of Artificial Sequence: primer

<400> SEQUENCE: 1

```
gtaccatcat atatgtccgt gctagaagga aacagttaca                          40

<210> SEQ ID NO 2
<211> LENGTH: 80
<212> TYPE: DNA
<213> ORGANISM: Artificial Sequence
<220> FEATURE:
<223> OTHER INFORMATION: Description of Artificial Sequence:  primer

<400> SEQUENCE: 2
tagcacggac atatatgatg gtaccgcagt atgagtatct cctatcacta ctaagtggaa   60
gaaatgtaac tgtttccttc                                               80

<210> SEQ ID NO 3
<211> LENGTH: 18
<212> TYPE: DNA
<213> ORGANISM: Artificial Sequence
<220> FEATURE:
<221> NAME/KEY: misc_feature
<222> LOCATION: (1)
<223> OTHER INFORMATION: Cy3 Fluorescent label at 5' end
<220> FEATURE:
<221> NAME/KEY: misc_feature
<222> LOCATION: (18)
<223> OTHER INFORMATION: Description of Artificial Sequence: detection
      probe
<220> FEATURE:
<223> OTHER INFORMATION: Cy3 Fluorescent label at 3' end

<400> SEQUENCE: 3
tatatgatgg taccgcag                                                 18

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: detection
      probe
<220> FEATURE:
<221> NAME/KEY: misc_feature
<222> LOCATION: (1)
<223> OTHER INFORMATION: Cy3 Fluorescent label at 5' end
<220> FEATURE:
<221> NAME/KEY: misc_feature
<222> LOCATION: (18)
<223> OTHER INFORMATION: Cy3 Fluorescent label at 3' end

<400> SEQUENCE: 4
tgagtatctc ctatgact                                                 18

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: detection
      probe
<220> FEATURE:
<221> NAME/KEY: misc_feature
<222> LOCATION: (1)
<223> OTHER INFORMATION: Cy3 Fluorescent label at 5' end
<220> FEATURE:
<221> NAME/KEY: misc_feature
<222> LOCATION: (18)
<223> OTHER INFORMATION: Cy3 Fluorescent label at 3' end

<400> SEQUENCE: 5
taagtggaag aaatgtaa                                                 18
```

```
<210> SEQ ID NO 6
<211> LENGTH: 40
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 6
gtaccatcat atatgtccgt gctagaagga aacagttaca                              40

<210> SEQ ID NO 7
<211> LENGTH: 35
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 7
aaaaaaaaaa aaaaacacag ctgaggatag gacat                                   35

<210> SEQ ID NO 8
<211> LENGTH: 80
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 8
tagcacggac atatatgatg gtaccgcagt atgagtatct cctatcacta ctaagtggaa        60
gaaatgtaac tgtttccttc                                                    80
```

US 6,921,642 B2

PROTEIN EXPRESSION PROFILING

CROSS-REFERENCE TO RELATED APPLICATIONS

This application is a continuation of application Ser. No. 09/597,836, filed Jun. 20, 2000, now U.S. Pat. No. 6,531,283 entitled "Protein Expression Profiling," by Stephen Kingsmore, Girish Nallur, and Barry Schweitzer, which is hereby incorporated herein by reference in its entirety.

FIELD OF THE INVENTION

The disclosed invention is generally in the area of detection and profiling of proteins and peptides, and specifically in the area of microscale protein expression profiling.

BACKGROUND OF THE INVENTION

The information content of the genome is carried as deoxyribonucleic acid (DNA). The size and composition of a given genomic sequence determines the form and function of the resultant organism. In general, genomic complexity is proportional to the complexity of the organism. Relatively simple organisms such as bacteria have genomes of about 1–5 megabases while mammalian genomes are approximately 3000 megabases. The genome is generally divided into distinct segments known as chromosomes. The bacterium *Escherichia coli* (*E. coli*) contains a single circular chromosome, whereas the human genome consists of 24 chromosomes.

Genomic DNA exists as a double-stranded polymer containing four DNA bases (A, G, C, and T) tethered to a sugar-phosphate backbone. The order of the bases along the DNA is the primary sequence of the DNA. The genome of an organism contains both protein coding and non-coding regions, including exons and introns, promoter and gene regulatory regions, and non-functional DNA. Genome analysis can provide a quantitative measure of gene copy number and chromosome number, as well as the presence of single base differences in the primary sequence of the DNA. Single base changes that are inherited are referred to as polymorphisms, whereas those that are acquired during the life of an organism are known as mutations. Genomic analysis at the DNA level does not provide a measure of gene expression (that is, the process by which RNA and protein copies of the coding sequences are synthesized).

All of the cells from a given organism are assumed to contain identical genomes, while genomes from different individuals of the same species are typically about 99.9% identical. The 0.1% polymorphism rate among individuals (Wang et al., *Science* 280: 1077 (1998)) is significant in that approximately three million polymorphisms are expected to be found upon complete sequencing of any two human genomes. If single base changes occur in protein coding segments, polymorphisms can alter the protein sequence and therefore change the biochemical activity of the protein.

The DNA genome consists of discrete functional regions known as genes. Genomes of simple organisms such as bacteria contain approximately 1000 genes (Fleischmann et al., *Science* 269: 496 (1995)), whereas the human genome is estimated to contain about 100,000 genes (Fields et al., *Nature Genet.* 7: 345 (1994)). Genomic analysis at the mRNA level can be used as a measure of gene expression. Expression levels for each gene are determined by a combination of genetic and environmental factors. The genetic factors include the precise DNA sequence of gene regulatory regions such as promoters, enhancers, and splice sites. Polymorphisms in the DNA are thus expected to contribute some of the differences in gene expression among individuals of the same species. Expression levels are also affected by environmental factors, including temperature, stress, light, and signals that lead to changes in the levels of hormones and other signaling substances. For this reason, RNA analysis provides information not only about the genetic potential of an organism, but also about changes in functional state (M. Schena and R. W. Davis, *DNA Microarrays: A Practical Approach*. (Oxford University Press, New York, 1999) 1–16.)

The second step in gene expression is the synthesis of protein from mRNA. A unique protein is encoded by each mRNA, such that every three nucleotides of mRNA encodes one amino acid of the polypeptide chain, with the linear order of the nucleotides represented as a linear sequence of amino acids. Once synthesized, the protein assumes a unique three-dimensional conformation that is determined largely by the primary amino acid sequence. Proteins impart the functional instructions of the genome by performing a wide range of biochemical activities including roles in gene regulation, metabolism, cell structure, and DNA replication.

Individuals in a population may have differences in protein activity due to polymorphisms that either alter the primary amino acid sequence of the proteins or perturb steady state protein levels by altering gene expression. Similar to mRNA levels, protein levels can also change in response to changes in the environment; moreover, protein levels are also subject to translational and post-translational control which do not effect mRNA levels directly (Schena and David, 1999). Proteomics analysis provides data on when or if a predicted gene product is actually translated, the level and type of post-translational modification it may undergo and its relative concentration compared with other proteins (Humphrey-Smith and Blackstock, *J. Protein. Chem.* 16: 537–544 (1997)). After DNA is transcribed into mRNA, the exons may be spliced in different ways before being translated into proteins. Following the translation of mRNA by ribosomes, proteins are usually post-translationally modified by the addition of different chemical groups such as carbohydrate, lipid and phosphate groups, as well as through the proteolytic cleavage of specific peptide bonds. These chemical modifications are crucial to modulating protein function but are not directly coded for by genes. Furthermore, both mRNA and protein are continually being synthesized and degraded, and thus final levels of protein are not easily obtainable by measuring mRNA levels (Patton, *J. Chromatogr.* 722: 203–223, (1999); Patton et al., *J. Biol. Chem.* 270: 21404–21410 (1995)). So while mRNA levels are often extrapolated to indicate the levels of expressed proteins, it is not surprising that there is little correlation between the abundance of mRNA species and the actual amounts of proteins that they code for (Anderson and Seilhamer, *Electrophoresis* 18: 533–537; Gygi et al., *Mol. Cell. Biol.* 19: 1720–1730 (1999)).

A growing body of evidence suggests that changes in gene and protein expression may correlate with the onset of a given human disease (Schena and Davis, 1999). Proteomic analysis of disease tissues should allow the identification of proteins whose expression is altered in a given illness. Many small molecules may also alter protein expression at a global level. Combining information about altered expression in a disease state with the changes that result from treatment with a small molecule would provide valuable information about classes of molecules that may be effective in combating a given disease. Proteomics thus has a role in processes such as lead compound screening and optimization, toxicity, pharmacodynamics, and drug efficacy.

A pivotal component of proteomics is its ability to accurately quantify vast numbers of proteins accurately and reproducibly. Typically, proteomics entails the simultaneous separation of proteins from a biological sample, and the quantitation of the relative abundance of the proteins resolved during the separation. Proteomics currently relies heavily on two-dimensional (2-D) gel electrophoresis. However, obtaining information concerning global protein expression using 2-D gels is technically difficult, and semi-automated procedures to carry out this process are in their infancy (Patton, *Biotechniques* 28: 944–957 (2000)). Furthermore, the commonly used stains for evaluating protein expression in 2-D gels (such as Coomassie Blue, colloidal gold and silver stain) do not provide the requisite dynamic range to be effective in this capacity. These stains are linear over only a 10- to 40-fold range, whereas the abundance of individual proteins differs by as much as four orders of magnitude (Brush, *The Scientist* 12:16–22, 1998; Wirth and Romano, *J. Chromatogr* 698: 123–143 (1995)). In addition, low abundance proteins, such as transcription factors and kinases that are present in 1–2000 copies per cell, often represent species that perform important regulatory functions. The accurate detection of such low-abundance proteins is an important challenge to proteomics. Methods have recently been introduced to directly quantify the relative abundance of proteins in two different samples by mass spectrometry. However, the linear dynamic range of these methods has been demonstrated over only a four- to ten-fold range (Gygi et al. 1999; Oda et al., *Proc. Natl. Acad. Sci USA* 96: 6591–6596 (1999)).

It has been noted recently that developing microarray technologies would make possible the simultaneous, ultrasensitive measurement of hundreds or even thousands of substances in a small sample (Ekins, *Clin. Chem.* 44: 2015–2030 (1998)). This approach has been difficult to reduce to practice, however, because the extremely small volumes (about 0.5–5 nl) of sample used to create spots on these microarrays makes it necessary to utilize methods of analyte detection that are extremely sensitive. Rolling Circle Amplification (RCA) driven by DNA polymerase can replicate circular oligonucleotide probes with either linear or geometric kinetics under isothermal conditions (Lizardi et al., *Nature Genet.* 19: 225–232 (1998)). If a single primer is used, RCA generates in a few minutes a linear chain of hundreds or thousands of tandemly-linked DNA copies of a target which is covalently linked to that target. Generation of a linear amplification product permits both spatial resolution and accurate quantitation of a target. DNA generated by RCA can be labeled with fluorescent oligonucleotide tags that hybridize at multiple sites in the tandem DNA sequences. RCA can be used with fluorophore combinations designed for multiparametric color coding (Speicher et al., *Nature Genet.* 12:368–375 (1996)), thereby markedly increasing the number of targets that can be analyzed simultaneously. RCA technologies can be used in solution, in situ and in microarrays. In solid phase formats, detection and quantitation can be achieved at the level of single molecules (Lizardi et al., 1998).

It is therefore an object of the present invention to provide a method for detecting small quantities and concentrations of analytes.

It is a further object of the present invention to provide a method for detecting small quantities and concentrations of multiple analytes in samples.

It is a further object of the present invention to provide a method for amplifying the signal of an analyte to be detected.

It is a further object of the present invention to provide an automated method for detecting small quantities and concentrations of multiple analytes in samples.

It is a further object of the present invention to provide a method for profiling the presence of multiple analytes in a sample.

It is a further object of the present invention to provide a method for comparing profiles of the presence of multiple analytes in different samples.

It is a further object of the present invention to provide a method for assessing the interaction of compounds with molecules of interest.

It is a further object of the present invention to provide a method for detecting small quantities and concentrations of proteins and peptides.

It is a further object of the present invention to provide a method for detecting small quantities and concentrations of multiple proteins and peptides in samples.

It is a further object of the present invention to provide a method for amplifying the signal of a protein or peptide to be detected.

It is a further object of the present invention to provide an automated method for detecting small quantities and concentrations of multiple proteins and peptides in samples.

It is a further object of the present invention to provide a method for profiling the presence of multiple proteins and peptides in a sample.

It is a further object of the present invention to provide a method for comparing profiles of the presence of multiple proteins and peptides in different samples.

It is a further object of the present invention to provide a method for assessing the interaction of compounds with proteins and peptides of interest.

It is a further object of the present invention to provide compositions for detecting small quantities and concentrations of analytes.

It is a further object of the present invention to provide compositions for detecting small quantities and concentrations of proteins and peptides.

BRIEF SUMMARY OF THE INVENTION

Disclosed are compositions and methods for detecting small quantities of analytes such as proteins and peptides. The method involves associating nucleic acid primer with the analyte and subsequently using the primer to mediate rolling circle replication of a circular DNA molecule. Amplification of the DNA circle is dependent on the presence of the primer. Thus, the disclosed method produces an amplified signal, via rolling circle amplification, from any analyte of interest. The amplification is isothermic and can result in the production of a large amount of nucleic acid from each primer. The amplified DNA remains associated with the analyte, via the primer, and so allows spatial detection of the analyte.

The disclosed method is preferably used to detect and analyze proteins and peptides. In preferred embodiments, multiple proteins can be analyzed using microarrays with which multiple different proteins or analytes are directly or indirectly associated (if they are present in the sample being tested). A rolling circle replication primer is then associated with the various proteins using a conjugate of the primer and a specific binding molecule, such as an antibody, that is specific for the protein to be detected. Rolling circle replication primed by the primers results in production of a large amount of DNA at the site in the array where the proteins are immobilized. The amplified DNA serves as a readily detectable signal for the proteins. Different proteins in the array can be distinguished in several ways. For example, the location of the amplified DNA can indicate the protein involved if different proteins are immobilized at predetermined locations in the array. Alternatively, each different protein can be associated with a different rolling circle replication primer which in turn primes rolling circle replication of a different DNA circle. The result is distinctive amplified DNA for each different protein. The different amplified DNAs can be distinguished using any suitable sequence-based nucleic acid detection technique.

Another preferred embodiment of the disclosed method involves comparison of the proteins expressed in two or more different samples. The information generated is analogous to the type of information gathered in nucleic acid expression profiles. The disclosed method allows sensitive and accurate detection and quantitation of proteins expressed in any cell or tissue. The disclosed method also allows the same analyte(s) from different samples to be detected simultaneously in the same assay.

BRIEF DESCRIPTION OF THE DRAWINGS

FIGS. 18A and 18B are bar graphs of the amount of cytokines in simultaneous, multiplexed detection of two different cytokines on a microarray. The graphs show quantitation of IL1a as well as TNF cytokines from a sample containing a mixture of the two cytokines (FIG. 18A). Microarrays contained capture antibodies for the two cytokines immobilized at different locations in the array. Detection was performed by immunoRCA using an anti-biotin conjugated to primer 1. A control sample containing only IL1a produced a single signal, namely for IL1a, showing the specificity of the interaction (FIG. 18B).

DETAILED DESCRIPTION OF THE INVENTION

Figure 1:
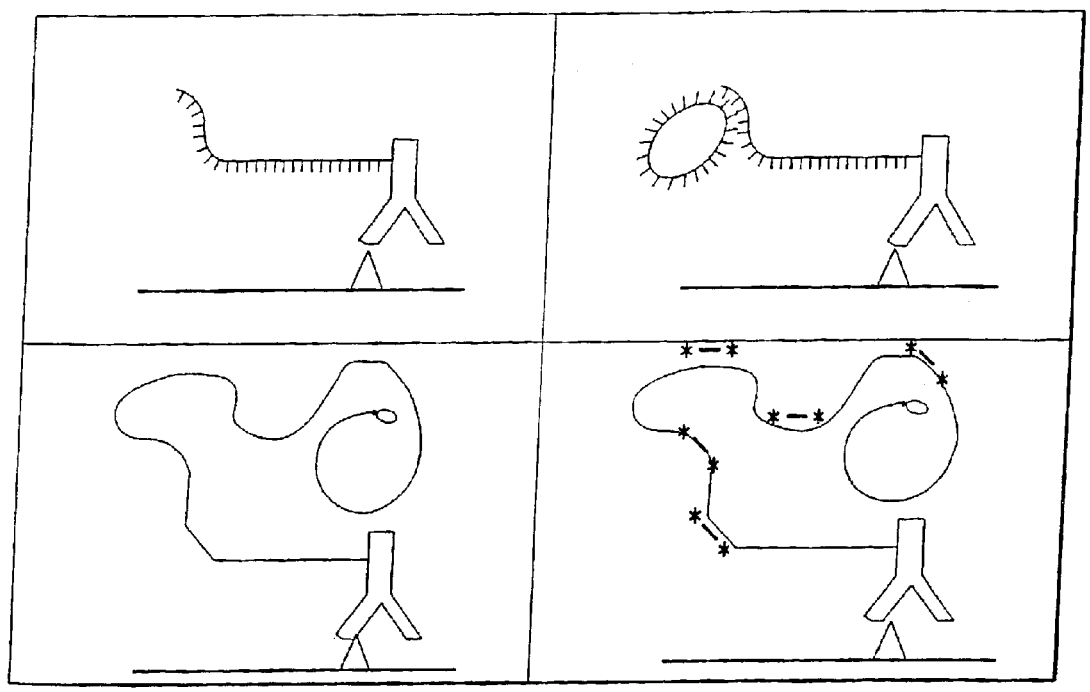
FIG. 1 is a diagram of an example of an immunoRCA assay. Top left: A reporter binding primer, made up of an antibody conjugated to an oligonucleotide) binds to an analyte that is captured on a solid surface by covalent attachment or by an analyte capture agent. Top right: An amplification target circle hybridizes to a complementary sequence in the oligonucleotide. Bottom left: The resulting complex is washed to remove excess reagents, and the amplification target circle is amplified by RCA. Bottom right: The amplified product is labeled in situ by hybridization with fluor-labeled oligonucleotides.

Disclosed are compositions and methods for detecting small quantities of analytes such as proteins and peptides. The method applies the power of nucleic acid signal amplification to the detection of non-nucleic acid analytes. Detection of such analytes—for which there are no amplification techniques comparable to nucleic acid amplification techniques—has generally depended on detection of sufficient quantities of the analyte or the use of extremely sensitive labels. The use of such labels is both cumbersome and limited. The disclosed method provides a simple and sensitive way to produce an amplified signal for any desired analyte.

The disclosed method is a form of RCA where a reporter binding primer provides the rolling circle replication primer for amplification of an amplification target circle. The disclosed method allows RCA to produce an amplified signal (that is, tandem sequence DNA (TS-DNA)) based on association of the reporter binding primer with a target molecule (also referred to as an analyte). The specific primer sequence that is a part of the reporter binding primer provides the link between the specific interaction of the reporter binding primer to a analyte (via the affinity portion of the reporter binding primer) and RCA. Once the reporter binding primer is associated with an analyte, an amplification target circle (ATC) is hybridized to the rolling circle replication primer sequence of the reporter binding primer, followed by amplification of the ATC by RCA. The resulting TS-DNA incorporates the rolling circle replication primer sequence of the reporter binding primer at one end, thus anchoring the TS-DNA to the site of the analyte. The disclosed method can be performed using any analyte. Preferred analytes are nucleic acids, including amplified nucleic acids such as TS-DNA and amplification target circles, antigens and ligands. Target molecules for the disclosed method are generally referred to herein as analytes.

The disclosed method is preferably used to detect and analyze proteins and peptides. In preferred embodiments, multiple proteins can be analyzed using microarrays to which the various proteins are immobilized (if they are present in the sample being tested). A rolling circle replication primer is then associated with the various proteins using a conjugate of the primer and a specific binding molecule, such as an antibody, that is specific for the protein to be detected. Rolling circle replication primed by the primers results in production of a large amount of DNA at the site in the array where the proteins are immobilized. The amplified DNA serves as a readily detectable signal for the proteins. Different proteins in the array can be distinguished in several ways. For example, the location of the amplified DNA can indicate the protein involved if different proteins are immobilized at pre-determined locations in the array. Alternatively, each different protein can be associated with a different rolling circle replication primer that in turn primes rolling circle replication of a different DNA circle. The result is distinctive amplified DNA for each different protein. The different amplified DNAs can be distinguished using any suitable sequence-based nucleic acid detection technique.

Another preferred embodiment of the disclosed method involves comparison of the proteins expressed in two or more different samples. The information generated is analogous to the type of information gathered in nucleic acid expression profiles. For example, the same analyte(s) from different samples can be associated with different primers which prime replication of different DNA circles to produce different amplified DNAs. In this way, an analyte from one sample will produce a different amplified DNA from the same analyte in a different sample. An example of this is shown in FIG. 11, where the same analyte from two different samples will result in amplification of two different DNA circles.

This sample-specific detection can be achieved even when the samples are mixed together following association of the primers with the analytes (a preferred mode of the method).

Figure 11:
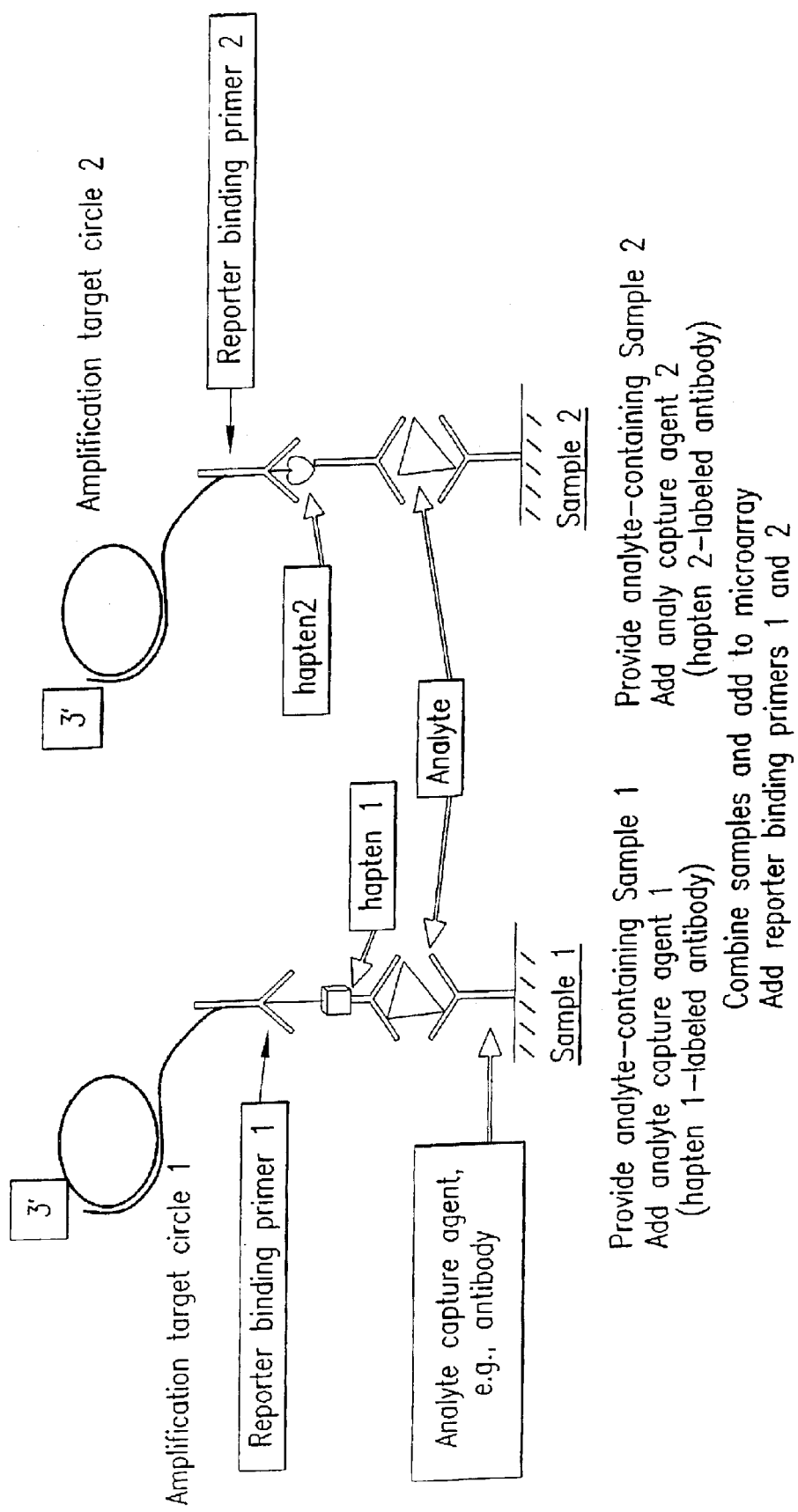
FIG. 11 is a diagram of an example of the disclosed method where the presence of the same analyte in two different samples (sample 1 and sample 2) can be detected in the same assay. This is accomplished by using two different analyte capture agents, each with a different capture portion (hapten 1 and hapten 2), such that a different reporter binding primer (reporter binding primers 1 and 2) will bind the different analyte capture agents. Each different reporter binding primer has a different rolling circle replication primer and thus each primer mediates rolling circle amplification of a different amplification target circle (amplification target circles 1 and 2).

For example, in FIG. 11, the analyte capture agents (the antibodies coupled to hapten 1 and hapten 2) can be mixed with sample 1 and sample 2, respectively. In another preferred embodiment, the analytes in each sample are labeled directly with different haptens. This associates a different hapten with the same type of analyte in the different samples. In preferred embodiments, the samples are mixed together. The analytes can be captured on substrate as shown in FIG. 11, reporter binding primers can be associated with the analyte capture agents, and DNA circles amplified from the rolling circle replication primers. Even if analytes from different samples are captured at the same location on the substrate (a preferred mode of the method), the source and amount of each analyte present at that location can be determined by virtue of the different amplified DNAs that will be produced.

The source of an analyte (that is, the sample from which the analyte came) can be determined, for example, by using different labels for different amplified DNAs (which resulted from primers keyed to the different samples). By using labels that can be distinguished when detected simultaneously with other labels (such as fluorescent labels with distinct emission spectra), all of the samples can be mixed together and analyzed together. The detected label identifies the source of the analyte indirectly through the chain of components: label to amplified DNA to circular DNA to primer to analyte.

In another preferred form of the disclosed method, referred to as ImmunoRCA, the 5 end of the rolling circle replication primer is attached to an antibody. In one preferred form of the disclosed method, the antibody is directed against a hapten. In another preferred form of the disclosed method, the antibody is directed against the analyte itself. In the presence of circular DNA (referred to as an amplification target circle), DNA polymerase, and nucleotides, the rolling circle reaction results in a DNA molecule consisting of multiple copies of the circle DNA sequence (referred to as tandem sequence DNA) that remains attached to the antibody (FIG. 1). The amplified DNA can be detected in a variety of ways, including direct incorporation of hapten- or fluorescently-labeled nucleotides, or by hybridization of fluor or enzymatically labeled complementary oligonucleotide probes. Although RCA reactions can be carried out with either linear or geometric kinetics (Lizardi et al., 1998), the disclosed signal-generation method preferably uses linear RCA.

In another aspect, the disclosed method involves immobilization of analytes present in complex biological samples and determining and quantitating their presence in the samples. The process of identifying and quantitating analytes by immobilization is described herein using samples containing allergens. For example, allergens present in biological extracts and fluids can be identified by first selectively immobilizing them on microarrays as described in Example 8. An immunoRCA microarray assay can then be employed for detection and quantitation.

In another aspect, the disclosed method involves multiplexed detection and quantitation of more than one analytes in a sample. This is illustrated in Example 9 where a microarray containing several test sites, each test site containing an immobilized capture antibody was incubated with sample containing a mixture of protein analytes to be detected. The microarrays were next incubated with a mixture containing at least one biotinylated antibody for each analyte. An immunoRCA microarray assay was then employed for detection and quantitation.

In another aspect, an immunoRCA microarray assay can be performed in 16 microwell-glass slides, wherein each well is separated by a Teflon mask. This is illustrated in Example 8 where microarrays of 100–400 spots were printed in each microwell. Each of these wells was used to assay different samples, and controls. Multiwell slides were also printed with arrays of anti-IgE capture antibodies in 6 of the 16 wells. Semi-automation of immunoRCA assays on allergen microarrays in this multiwell format can be implemented, for example, on an inexpensive Beckman BioMek liquid handling robot.

Microarray-based immunoRCA assay can be applied to other multiplexed antibody assays. For example, certain immunological reactions are caused by specific $IgG_4$ rather than IgE (AAAI Board of Directors, *J Allergy Clin Immunol.* 95:652–654 (1995)). The use of an anti-human $IgG_4$ conjugated to a DNA primer complementary to a DNA circle that is different in sequence from the DNA circle to which the primer conjugated to an anti-IgE is complementary would allow the simultaneous measurement of allergen-specific $IgG_4$ and IgE. Such an assay can be used during allergen desensitisation therapy or for monitoring response to anti-IgE therapy (Chang *Nature Biotech.* 18:157–162 (2000)).

The enormous multiplexing capabilities of immunoRCA on microarrays, both spatial (i.e. the ability to spot multiple analytes on the array) and colorometric (i.e. the ability to detect and differentiate multiple antibody types binding to each analyte) can be used for other clinical diagnostic tests involving detection of multiple specific antibodies, such as autoantibodies in suspected systemic autoimmune disorders, inflammatory arthritis, organ-specific autoimmune disorders or, indeed, in histocompatibility testing. Additional applications include infectious disease diagnostics with measurement of strain- and species-specific IgM and IgG, as well as in vitro testing of functional antibody responses in patients with suspected primary and secondary immunodeficiency diseases. Finally, the multiplexing, automation and ultrasensitivity of this format can be applied to other immunoassays besides those involving antibody detection. RCA-powered sandwich immunoassays on microarrays can provide a 3- to 4-log gain in sensitivity over conventional assays for analytes such as prostate serum antigen. Thus, the disclosed method produces a huge gain in diagnostic and prognostic power made possible by the simultaneous testing of multiple analytes for the molecular staging of disease.

Nucleic acids are ideal molecular labels for multiple analyte detection because different specific sequences can be arbitrarily associated with each individual analyte. Direct covalent coupling of DNA to antibody permits an unlimited number of antibody-DNA adducts to be prepared and used in any combination, provided that each DNA label is unique (Hendrickson et al., *Nucleic Acids Res.* 23: 522–529 (1995)). Covalent coupling also has advantages for the implementation of simple assay formats, since fewer reagent mixing and washing steps are required; furthermore, variability in the stoichiometry of the assembled components can be avoided. In preferred embodiments, the disclosed method uses a covalent coupling strategy in a signal amplification strategy, termed ImmunoRCA. By employing several modifications and improvements in the synthetic and purification strategies, these conjugates can be produced in high yields with a high degree of purity.

Materials

A. Analytes

The disclosed method involves the detection of analytes. In general, any compound, moiety, or component of a compound or complex can be an analyte. Preferred analytes are peptides, proteins, and other macromolecules such as lipids, complex carbohydrates, proteolipids, membrane fragments, and nucleic acids. Analytes can also be smaller molecules such as cofactors, metabolites, enzyme substrates, metal ions, and metal chelates. Analytes preferably range in size from 100 daltons to 1,000,000 daltons.

Analytes may contain modifications, both naturally occurring or induced in vitro or in vivo. Induced modifications include adduct formation such as hapten attachment, multimerization, complex formation by interaction with other chemical moieties, digestion or cleavage (by, for example, protease), and metal ion attachment or removal. The disclosed method can be used to detect differences in the modification state of an analyte, such as the phosphorylation or glycosylation state of proteins.

Analytes can be associated directly or indirectly with substrates, preferably in arrays. Most preferred are microarrays. Analytes can be captured and/or immobilized using analyte capture agents. Immobilized analytes can be used to capture other components used in the disclosed method such as analyte capture agents and reporter binding primers.

B. Reporter Binding Primers

A reporter binding primer is a specific binding molecule coupled or tethered to an oligonucleotide. The specific binding molecule is referred to as the affinity portion of the reporter binding primer and the oligonucleotide is referred to as the oligonucleotide portion of the reporter binding primer. In the disclosed method the oligonucleotide portion serves as a rolling circle replication primer (accordingly, the oligonucleotide portion of reporter binding agents are also referred to herein as a rolling circle replication primer). This allows rolling circle replication of an added ATC where the resulting TS-DNA is coupled to the reporter binding primer. Because of this, the TS-DNA will be effectively immobilized at the site of the analyte.

The sequence of the rolling circle replication primer sequence can be arbitrarily chosen. In a multiplex assay using multiple reporter binding primers, it is preferred that the rolling circle replication primer sequence for each reporter binding primer be substantially different to limit the possibility of non-specific target detection. Alternatively, it may be desirable in some multiplex assays, to use rolling circle replication primer sequences with related sequences. Such assays can use one or a few ATCs to detect a larger number of analytes. The oligonucleotide portion can be any length that supports specific and stable hybridization between the oligonucleotide portion and the primer complement portion of an amplification target circle. Generally this is 12 to 100 nucleotides long, but is preferably 20 to 45 nucleotides long.

As used herein, a specific binding molecule is a molecule that interacts specifically with a particular molecule or moiety. The molecule or moiety that interacts specifically with a specific binding molecule can be an analyte or another molecule that serves as an intermediate in the interaction between the specific binding molecule and the analyte. A preferred example of such an intermediate is an analyte capture agent. It is to be understood that the term analyte refers to both separate molecules and to portions of molecules, such as an epitope of a protein, that interacts specifically with a specific binding molecule. Antibodies, either member of a receptor/ligand pair, and other molecules with specific binding affinities are examples of specific binding molecules, useful as the affinity portion of a reporter binding primer. A reporter binding primer with an affinity portion that is an antibody is also referred to herein as a reporter antibody. By coupling a rolling circle replication primer to such specific binding molecules, binding of a specific binding molecule to its specific target can be detected by amplifying an ATC with rolling circle amplification. This amplification allows sensitive detection of a very small number of bound analytes.

A reporter binding primer that interacts specifically with a particular analyte is said to be specific for that analyte. For example, a reporter binding primer with an affinity portion that is an antibody that binds to a particular antigen is said to be specific for that antigen. The antigen is the analyte.

Antibodies useful as the affinity portion of reporter binding primers, can be obtained commercially or produced using well established methods. For example, Johnstone and Thorpe, on pages 30–85, describe general methods useful for producing both polyclonal and monoclonal antibodies. The entire book describes many general techniques and principles for the use of antibodies in assay systems.

In use, the reporter binding primers need not be absolutely pure. The reporter binding primers preferably are at least 20% pure, more preferably at least 50% pure, more preferably at least 80% pure, and more preferably at least 90% pure.

C. Amplification Target Circles

An amplification target circle (ATC) is a circular single-stranded DNA molecule, generally containing between 40 to 1000 nucleotides, preferably between about 50 to 150 nucleotides, and most preferably between about 50 to 100 nucleotides. Portions of ATCs have specific functions making the ATC useful for rolling circle amplification (RCA). These portions are referred to as the primer complement portion, the detection tag portions, the secondary target sequence portions, the address tag portions, and the promoter portion. The primer complement portion is a required element of an amplification target circle. Detection tag portions, secondary target sequence portions, address tag portions, and promoter portions are optional. Generally, an amplification target circle is a single-stranded, circular DNA molecule comprising a primer complement portion. Those segments of the ATC that do not correspond to a specific portion of the ATC can be arbitrarily chosen sequences. It is preferred that ATCs do not have any sequences that are self-complementary. It is considered that this condition is met if there are no complementary regions greater than six nucleotides long without a mismatch or gap. It is also preferred that ATCs containing a promoter portion do not have any sequences that resemble a transcription terminator, such as a run of eight or more thymidine nucleotides.

An amplification target circle, when replicated, gives rise to a long DNA molecule containing multiple repeats of sequences complementary to the amplification target circle. This long DNA molecule is referred to herein as tandem sequences DNA (TS-DNA). TS-DNA contains sequences complementary to the primer complement portion and, if present on the amplification target circle, the detection tag portions, the secondary target sequence portions, the address tag portions, and the promoter portion. These sequences in the TS-DNA are referred to as primer sequences (which match the sequence of the rolling circle replication primer), spacer sequences (complementary to the spacer region), detection tags, secondary target sequences, address tags, and promoter sequences. Amplification target circles are useful as tags for specific binding molecules.

D. Rolling Circle Replication Primer

A rolling circle replication primer (RCRP) is an oligonucleotide having sequence complementary to the primer complement portion of an ATC. This sequence is referred to as the complementary portion of the RCRP. The complementary portion of a RCRP and the cognate primer complement portion can have any desired sequence so long as they are complementary to each other. In general, the sequence of the RCRP can be chosen such that it is not significantly complementary to any other portion of the ATC. The complementary portion of a rolling circle replication primer can be any length that supports specific and stable hybridization between the primer and the primer complement portion. Generally this is 12 to 100 nucleotides long, but is preferably 20 to 45 nucleotides long.

It is preferred that rolling circle replication primers also contain additional sequence at the 5' end of the RCRP that is not complementary to any part of the ATC. This sequence is referred to as the non-complementary portion of the RCRP. The non-complementary portion of the RCRP, if present, serves to facilitate strand displacement during DNA replication. The non-complementary portion of a RCRP may be any length, but is generally 1 to 100 nucleotides long, and preferably 4 to 8 nucleotides long. A rolling circle replication primer can be used as the tertiary DNA strand displacement primer in strand displacement cascade amplification.

In preferred embodiments, rolling circle replication primers (and other primers used in the method) can contain a spacer. The spacer can help to overcome steric factors from the surface when immobilized, aid in anchoring polymerase on primers, or provide other advantages, such as control or alteration of the hydrophobicity of array elements. Spacers useful for the disclosed method include nucleotide spacers such as poly dT or poly dA; aliphatic linkers such as C18, C12, or multimers thereof; aromatic spacers, or RNA, DNA, PNA or combinations thereof.

E. Analyte Capture Agents

An analyte capture agent is any compound that can interact with an analyte and allow the analyte to be immobilized or separated from other compounds and analytes. An analyte capture agent includes an analyte interaction portion. Analyte capture agents can also include a capture portion. Analyte capture agents without a capture portion preferably are immobilized on a solid support. The analyte interaction portion of an analyte capture agent is a molecule that interacts specifically with a particular molecule or moiety. The molecule or moiety that interacts specifically with an analyte interaction portion can be an analyte or another molecule that serves as an intermediate in the interaction between the analyte interaction portion and the analyte. It is to be understood that the term analyte refers to both separate molecules and to portions of molecules, such as an epitope of a protein, that interacts specifically with an analyte interaction portion. Antibodies, either member of a receptor/ligand pair, and other molecules with specific binding affinities are examples of molecules that can be used as an analyte interaction portion of an analyte capture agent. The specific binding portion of an analyte capture agent can also be any compound or composition with which an analyte can interact, such as peptides. An analyte capture agent that interacts specifically with a particular analyte is said to be specific for that analyte. For example, an analyte capture agent with an analyte interaction portion that is an antibody that binds to a particular antigen is said to be specific for that antigen. The antigen is the analyte.

Examples of molecules useful as the analyte interaction portion of analyte capture agents are antibodies, such as crude (serum) antibodies, purified antibodies, monoclonal antibodies, polyclonal antibodies, synthetic antibodies, antibody fragments (for example, Fab fragments); antibody interacting agents, such as protein A, carbohydrate binding proteins, and other interactants; protein interactants (for example avidin and its derivatives); peptides; and small chemical entities, such as enzyme substrates, cofactors, metal ions/chelates, and haptens. Antibodies may be modified or chemically treated to optimize binding to surfaces and/or targets.

Antibodies useful as the analyte interaction portion of analyte capture agents, can be obtained commercially or produced using well-established methods. For example, Johnstone and Thorpe, on pages 30–85, describe general methods useful for producing both polyclonal and monoclonal antibodies. The entire book describes many general techniques and principles for the use of antibodies in assay systems.

The capture portion of an analyte capture agent is any compound that can be associated with another compound. Preferably, a capture portion is a compound, such as a ligand or hapten, that binds to or interacts with another compound, such as ligand-binding molecule or an antibody. It is also preferred that such interaction between the capture portion and the capturing component be a specific interaction, such as between a hapten and an antibody or a ligand and a ligand-binding molecule. Examples of haptens include biotin, FITC, digoxigenin, and dinitrophenol. The capture portion can be used to separate compounds or complexes associated with the analyte capture agent from those that do not.

Capturing analytes or analyte capture agents on a substrate may be accomplished in several ways. In one embodiment, capture docks are adhered or coupled to the substrate. Capture docks are compounds or moieties that mediate adherence of an analyte by binding to, or interacting with, the capture portion on an analyte capture agent (with which the analyte is, or will be, associated). Capture docks immobilized on a substrate allow capture of the analyte on the substrate. Such capture provides a convenient means of washing away reaction components that might interfere with subsequent steps. Alternatively, analyte capture agents can be directly immobilized on a substrate. In this case, the analyte capture agent need not have a capture portion.

In one embodiment, the analyte capture agent or capture dock to be immobilized is an anti-hybrid antibody. Methods for immobilizing antibodies and other proteins to substrates are well established. Immobilization can be accomplished by attachment, for example, to aminated surfaces, carboxylated surfaces or hydroxylated surfaces using standard immobilization chemistries. Examples of attachment agents are cyanogen bromide, succinimide, aldehydes, tosyl chloride, avidin-biotin, photocrosslinkable agents, epoxides and maleimides. A preferred attachment agent is a heterobifunctional cross-linking agent such as N-[γ-maleimidobutyryloxy]succinimide ester (GMBS). These and other attachment agents, as well as methods for their use in attachment, are described in *Protein immobilization: fundamentals and applications*, Richard F. Taylor, ed. (M. Dekker, New York, 1991), Johnstone and Thorpe, *Immunochemistry In Practice* (Blackwell Scientific Publications, Oxford, England, 1987) pages 209–216 and 241–242, and *Immobilized Affinity Ligands*, Craig T. Hermanson et al., eds. (Academic Press, New York, 1992). Antibodies can be attached to a substrate by chemically cross-linking a free amino group on the antibody to reactive side groups present within the substrate. For example, antibodies may be chemically cross-linked to a substrate that contains free amino, carboxyl, or sulfur groups using glutaraldehyde, carbodiimides, or heterobifunctional agents such as GMBS as cross-linkers. In this method, aqueous solutions containing free antibodies are incubated with the solid-state substrate in the presence of glutaraldehyde or carbodiimide. For crosslinking with glutaraldehyde the reactants can be incubated with 2% glutaraldehyde by volume in a buffered solution such as 0.1 M sodium cacodylate at pH 7.4. Other standard immobilization chemistries are known by those of skill in the art.

One useful form of analyte capture agents are peptides. When various peptides are immobilized in an array, they can be used as "bait" for analytes. For example, an array of different peptides can be used to access whether a sample has analytes that interact with any of the peptides. Comparisons of different samples can be made by, for example, noting differences in the peptides to which analytes in the different samples become associated. In another form of the disclosed method, an array of analyte capture agents specific for analytes of interest can be used to access the presence of a whole suite of analytes in a sample.

In use, the analyte capture agents need not be absolutely pure. The analyte capture agents preferably are at least 20% pure, more preferably at least 50% pure, more preferably at least 80% pure, and more preferably at least 90% pure.

F. Accessory Molecules

Accessory molecules are molecules that affect the interaction of analytes and specific binding molecules or analyte capture agents. For example, accessory molecules can be molecules that compete with the binding of an analyte with an analyte capture agent or specific binding molecule. One form of competitive accessory molecules are analogs of analytes. An analog is a molecule that is similar in structure but different in competition. In this context, the analyte analog should be sufficiently similar to interact with an analyte capture agent or specific binding molecule specific for that analyte. Accessory molecules can also be molecules that aid or are necessary for interaction of an analyte and a specific binding molecule or analyte capture agent. Such accessory molecules are referred to herein as analyte binding co-factors.

Figure 14:
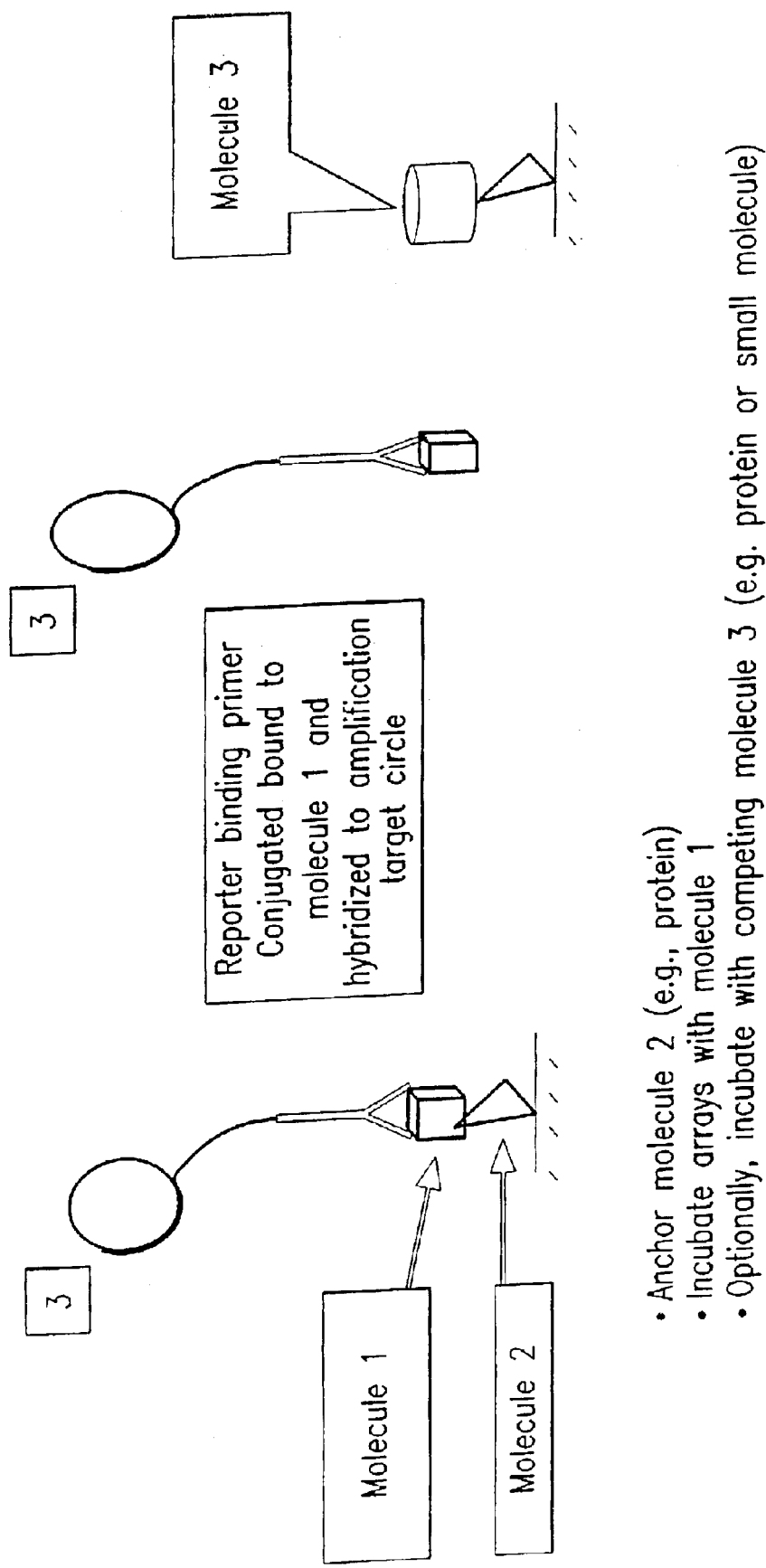
FIG. 14 is a diagram of an example of the disclosed method where the presence of a competitor molecule, or the ability of a molecule to compete with the interaction of two other molecules (molecule 1 and molecule 3), one of which is immobilized, is assessed. In the presence of an effective competitor molecule (molecule 3), interaction of the two other molecules is reduced or eliminated. A reporter binding primer is used that interacts with the non-immobilized molecule 1. If the two molecules interact, amplified DNA will be associated with the molecules. If not (that is, when the competitor molecule prevents interaction), amplified DNA will not be associated with the immobilized molecule. Molecules 1, 2, and 3 are an analyte, an analyte capture agent, and an accessory molecule in any order.
Figure 15:
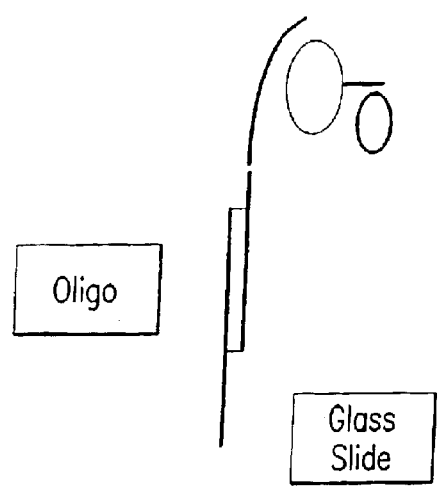
FIG. 15 is a diagram of an example of the disclosed method where interaction of a protein with a mRNA is detected. A reporter binding primer (ligand-primer) composed of a primer and a protein that interacts with mRNA is associated with mRNA and the mRNA/reporter binding primer conjugate (mRNA-peptide) is hybridized to a analyte capture agent (oligo) immobilized on a glass slide. The primer can then mediate rolling circle amplification.
Figure 16:
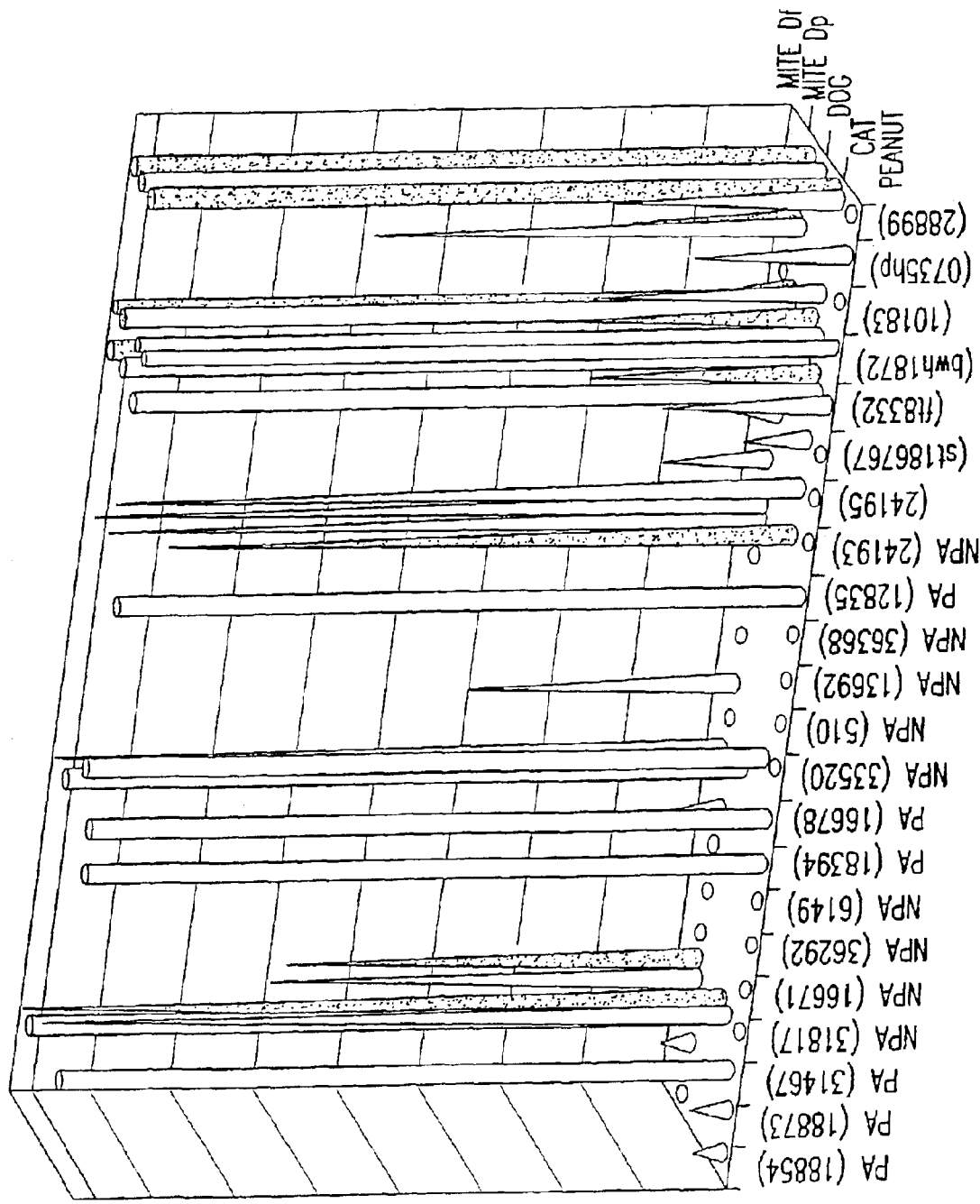
FIG. 16 is a bar graph of fluorescence intensity versus allergen on a microarray for a set of 22 patient samples. The graph shows immunoRCA microarray detection of allergen-specific IgE in patient sera. Serum samples from patients were incubated with microarrays spotted with extracts of cat hair, dog hair, house dust mite (*D. farinae* and *D. pteronyssinus*), and peanut as described in Example 8. Arrays were scanned and fluorescence signals were quantified as described.

In one form of the disclosed method, accessory molecules can be compounds that are to be tested for their effect on analyte binding. For example, the disclosed method can be used to screen for competitors (or binding co-factors) of an analyte interaction with a specific binding molecule or analyte capture agent. If an accessory molecule affects interaction of the analyte, the results of RCA will change since the association of the reporter binding primer to the analyte (or of the analyte capture agent to the analyte) will be lost or gained. An example of competition for interaction of an analyte and analyte capture agent is illustrated in FIG. 14.

In use, the accessory molecules need not be absolutely pure. The accessory molecules preferably are at least 20% pure, more preferably at least 50% pure, more preferably at least 80% pure, and more preferably at least 90% pure.

G. Detection Labels

To aid in detection and quantitation of nucleic acids amplified using the disclosed method, detection labels can be directly incorporated into amplified nucleic acids or can be coupled to detection molecules. As used herein, a detection label is any molecule that can be associated with amplified nucleic acid, directly or indirectly, and which results in a measurable, detectable signal, either directly or indirectly. Many such labels for incorporation into nucleic acids or coupling to nucleic acid or antibody probes are known to those of skill in the art. Examples of detection labels suitable for use in RCA are radioactive isotopes, fluorescent molecules, phosphorescent molecules, enzymes, antibodies, and ligands.

Examples of suitable fluorescent labels include fluorescein (FITC), 5,6-carboxymethyl fluorescein, Texas red, nitrobenz-2-oxa-1,3-diazol-4-yl (NBD), coumarin, dansyl chloride, rhodamine, 4'-6-diamidino-2-phenylinodole (DAPI), and the cyanine dyes Cy3, Cy3.5, Cy5, Cy5.5 and Cy7. Preferred fluorescent labels are fluorescein (5-carboxyfluorescein-N-hydroxysuccinimide ester) and rhodamine (5,6-tetramethyl rhodamine). Preferred fluorescent labels for combinatorial multicolor coding are FITC and the cyanine dyes Cy3, Cy3.5, Cy5, Cy5.5 and Cy7. The absorption and emission maxima, respectively, for these fluors are: FITC (490 nm; 520 nm), Cy3 (554 nm; 568 nm), Cy3.5 (581 nm; 588 nm), Cy5 (652 nm: 672 nm), Cy5.5 (682 nm; 703 nm) and Cy7 (755 nm; 778 nm), thus allowing their simultaneous detection. The fluorescent labels can be obtained from a variety of commercial sources, including Molecular Probes, Eugene, Oreg. and Research Organics, Cleveland, Ohio.

Labeled nucleotides are preferred form of detection label since they can be directly incorporated into the products of RCA during synthesis. Examples of detection labels that can be incorporated into amplified DNA or RNA include nucleotide analogs such as BrdUrd (Hoy and Schimke, *Mutation Research* 290:217–230 (1993)), BrUTP (Wansick et al., *J. Cell Biology* 122:283–293 (1993)) and nucleotides modified with biotin (Langer et al., *Proc. Natl. Acad. Sci. USA* 78:6633 (1981)) or with suitable haptens such as digoxygenin (Kerkhof, *Anal. Biochem.* 205:359–364 (1992)). Suitable fluorescence-labeled nucleotides are Fluorescein-isothiocyanate-dUTP, Cyanine-3-dUTP and Cyanine-5-dUTP (Yu et al., *Nucleic Acids Res.*, 22:3226–3232 (1994)). A preferred nucleotide analog detection label for DNA is BrdUrd (BUDR triphosphate, Sigma), and a preferred nucleotide analog detection label for RNA is Biotin-16-uridine-5'-triphosphate (Biotin-16-dUTP, Boehringher Mannheim). Fluorescein, Cy3, and Cy5 can be linked to dUTP for direct labeling. Cy3.5 and Cy7 are available as avidin or anti-digoxygenin conjugates for secondary detection of biotin- or digoxygenin-labeled probes.

Detection labels that are incorporated into amplified nucleic acid, such as biotin, can be subsequently detected using sensitive methods well-known in the art. For example, biotin can be detected using streptavidin-alkaline phosphatase conjugate (Tropix, Inc.), which is bound to the biotin and subsequently detected by chemiluminescence of suitable substrates (for example, chemiluminescent substrate CSPD: disodium, 3-(4-methoxyspiro-[1,2-dioxetane-3-2'-(5'-chloro)tricyclo [$3.3.1.1^{3,7}$]decane]-4-yl)phenyl phosphate; Tropix, Inc.).

A preferred detection label for use in detection of amplified RNA is acridinium-ester-labeled DNA probe (GenProbe, Inc., as described by Arnold et al., *Clinical Chemistry* 35:1588–1594 (1989)). An acridinium-ester-labeled detection probe permits the detection of amplified RNA without washing because unhybridized probe can be destroyed with alkali (Arnold et al. (1989)).

Molecules that combine two or more of these detection labels are also considered detection labels. Any of the known detection labels can be used with the disclosed probes, tags, and method to label and detect nucleic acid amplified using the disclosed method. Methods for detecting and measuring signals generated by detection labels are also known to those of skill in the art. For example, radioactive isotopes can be detected by scintillation counting or direct visualization; fluorescent molecules can be detected with fluorescent spectrophotometers; phosphorescent molecules can be detected with a scanner or spectrophotometer, or directly visualized with a camera; enzymes can be detected by detection or visualization of the product of a reaction catalyzed by the enzyme; antibodies can be detected by detecting a secondary detection label coupled to the antibody. Such methods can be used directly in the disclosed method of amplification and detection. As used herein, detection molecules are molecules that interact with amplified nucleic acid and to which one or more detection labels are coupled.

H. Detection Probes

Detection probes are labeled oligonucleotides having sequence complementary to detection tags on TS-DNA. The complementary portion of a detection probe can be any length that supports specific and stable hybridization between the detection probe and the detection tag. For this purpose, a length of 10 to 35 nucleotides is preferred, with a complementary portion of a detection probe 16 to 20 nucleotides long being most preferred. Detection probes can contain any of the detection labels described above. Preferred labels are biotin and fluorescent molecules. A particularly preferred detection probe is a molecular beacon. Molecular beacons are detection probes labeled with fluorescent moieties where the fluorescent moieties fluoresce only when the detection probe is hybridized (Tyagi and Kramer, *Nature Biotechnology* 14:303–308 (1996)). The use of such probes eliminates the need for removal of unhybridized probes prior to label detection because the unhybridized detection probes will not produce a signal. This is especially useful in multiplex assays. The TS-DNA can be collapsed as described in WO 97/19193 using collapsing detection probes. Collapsing TS-DNA is especially useful with combinatorial multicolor coding, which is described below.

I. DNA Strand Displacement Primers

Primers used for secondary DNA strand displacement are referred to herein as DNA strand displacement primers. One form of DNA strand displacement primer, referred to herein as a secondary DNA strand displacement primer, is an oligonucleotide having sequence matching part of the sequence of an ATC. This sequence is referred to as the matching portion of the secondary DNA strand displacement primer. This matching portion of a secondary DNA strand displacement primer is complementary to sequences in TS-DNA. The matching portion of a secondary DNA strand displacement primer may be complementary to any sequence in TS-DNA. The matching portion of a secondary DNA strand displacement primer can be any length that supports specific and stable hybridization between the primer and its complement. Generally this is 12 to 35 nucleotides long, but is preferably 18 to 25 nucleotides long.

Another form of DNA strand displacement primer, referred to herein as a tertiary DNA strand displacement primer, is an oligonucleotide having sequence complementary to part of the sequence of an ATC. This sequence is referred to as the complementary portion of the tertiary DNA strand displacement primer. This complementary portion of the tertiary DNA strand displacement primer matches sequences in TS-DNA. The complementary portion of a tertiary DNA strand displacement primer may be complementary to any sequence in the ATC. The complementary portion of a tertiary DNA strand displacement primer can be any length that supports specific and stable hybridization between the primer and its complement. Generally this is 12 to 35 nucleotides long, but is preferably 18 to 25 nucleotides long.

DNA strand displacement primers and their use are described in more detail in U.S. Pat. No. 5,854,033 and WO 97/19193.

J. Oligonucleotide Synthesis

Rolling circle replication primers, detection probes, address probes, amplification target circles, DNA strand displacement primers, and any other oligonucleotides can be synthesized using established oligonucleotide synthesis methods. Methods to produce or synthesize oligonucleotides are well known in the art. Such methods can range from standard enzymatic digestion followed by nucleotide fragment isolation (see for example, Sambrook et al., *Molecular Cloning: A Laboratory Manual,* 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or PerSeptive Expedite). Synthetic methods useful for making oligonucleotides are also described by Ikuta et al., *Ann. Rev. Biochem.* 53:323–356 (1984), (phosphotriester and phosphite-triester methods), and Narang et al., *Methods Enzymol.,* 65:610–620 (1980), (phosphotriester method). Protein nucleic acid molecules can be made using known methods such as those described by Nielsen et al., *Bioconjug. Chem.* 5:3–7 (1994).

Many of the oligonucleotides described herein are designed to be complementary to certain portions of other oligonucleotides or nucleic acids such that stable hybrids can be formed between them. The stability of these hybrids can be calculated using known methods such as those described in Lesnick and Freier, *Biochemistry* 34:10807–10815 (1995), McGraw et al., *Biotechniques* 8:674–678 (1990), and Rychlik et al., *Nucleic Acids Res.* 18:6409–6412 (1990).

K. Solid Supports

Solid supports are solid-state substrates or supports with which analytes can be associated. Analytes can be associated with solid supports directly or indirectly. For example, analytes can be directly immobilized on solid supports. Analyte capture agents and accessory molecules can also be immobilized on solid supports. A preferred form of solid support is an array. Another form of solid support is an array detector. An array detector is a solid support to which multiple different address probes or detection molecules have been coupled in an array, grid, or other organized pattern.

Solid-state substrates for use in solid supports can include any solid material to which oligonucleotides can be coupled. This includes materials such as acrylamide, agarose, cellulose, nitrocellulose, glass, polystyrene, polyethylene vinyl acetate, polypropylene, polymethacrylate, polyethylene, polyethylene oxide, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, and polyamino acids. Solid-state substrates can have any useful form including thin film, membrane, bottles, dishes, fibers, woven fibers, shaped polymers, particles, beads, microparticles, or a combination. Solid-state substrates and solid supports can be porous or non-porous. A preferred form for a solid-state substrate is a microtiter dish. The most preferred form of microtiter dish is the standard 96-well type. In preferred embodiments, a multiwell glass slide can be employed that normally contain one array per well. This feature allows for greater control of assay reproducibility, increased throughput and sample handling, and ease of automation.

Different analytes, analyte capture agents, or accessory molecules can be used together as a set. The set can be used as a mixture of all or subsets of the analytes, analyte capture agents, and accessory molecules used separately in separate reactions, or immobilized in an array. Analytes, analyte capture agents, and accessory molecules used separately or as mixtures can be physically separable through, for example, association with or immobilization on a solid support. An array includes a plurality of analytes, analyte capture agents and/or accessory molecules immobilized at identified or predefined locations on the array. Each predefined location on the array generally has one type of component (that is, all the components at that location are the same). Each location will have multiple copies of the component. The spatial separation of different components in the array allows separate detection and identification of analytes.

Although preferred, it is not required that a given array be a single unit or structure. The set of analytes, analyte capture agents, or accessory molecules may be distributed over any number of solid supports. For example, at one extreme, each probe may be immobilized in a separate reaction tube or container, or on separate beads or microparticles.

Different modes of the disclosed method can be performed with different components (for example, analytes, analyte capture agents, and accessory molecules) immobilized on a solid support. For example, FIG. 14 illustrates a form of the disclosed method where interactions between three molecules (molecules 1, 2, and 3) are assessed using a solid support. Each of the three molecules can represent, for example, an analyte capture reagent, and accessory molecule, or an analyte. If molecule 2 is an analyte, then molecule 1 would be an analyte capture agent and molecule 3 an accessory molecule. In this case, the analyte (molecule 2) is immobilized. If molecule 2 is an analyte capture agent, then molecule 1 would be an analyte and molecule 3 an accessory molecule. In this case, the analyte capture agent (molecule 2) is immobilized. In other forms of the method, the accessory molecule can be immobilized.

In alternative embodiments, RCA is performed in solution, and the products of the amplification are captured on an array. For example, a biotinylated capture antibody is added to a sample containing the analyte, followed by a reporter binding primer that binds to a different location on the analyte. These components—the capture antibody and the reporter binding primer—can be added in any order. RCA is then performed to produce TS-DNA, and purified on a matrix containing streptavidin (streptavidin beads (Dynal), for example). The TS-DNA is then detected or quantitated by hybridization to an array containing oligonucleotide probes complementary to the TS-DNA. Such probes are referred to herein as address probes. By attaching different address probes to different regions of a solid support, different RCA products can be captured at different, and therefore diagnostic, locations on the solid support. For example, in a microtiter plate multiplex assay, address probes specific for up to 96 different TS-DNAs (each amplified via different primers and ATCs) can be immobilized on a microtiter plate, each in a different well. Capture and detection will occur only in those probe elements in the array corresponding to TS-DNAs for which the corresponding analytes were present in a sample.

Methods for immobilization of oligonucleotides to solid-state substrates are well established. Oligonucleotides, including address probes and detection probes, can be coupled to substrates using established coupling methods. For example, suitable attachment methods are described by Pease et al., *Proc. Natl. Acad. Sci. USA* 91(11):5022–5026 (1994), and Khrapko et al., *Mol Biol (Mosk) (USSR)* 25:718–730 (1991). A method for immobilization of 3'-amine oligonucleotides on casein-coated slides is described by Stimpson et al., *Proc. Natl. Acad. Sci. USA* 92:6379–6383 (1995). A preferred method of attaching oligonucleotides to solid-state substrates is described by Guo et al., *Nucleic Acids Res.* 22:5456–5465 (1994).

Some solid supports useful in RCA assays have detection antibodies attached to a solid-state substrate. Such antibodies can be specific for a molecule of interest. Captured molecules of interest can then be detected by binding of a second, reporter antibody, followed by RCA. Such a use of antibodies in a solid support allows RCA assays to be developed for the detection of any molecule for which antibodies can be generated. Methods for immobilizing antibodies to solid-state substrates are well established. Immobilization can be accomplished by attachment, for example, to aminated surfaces, carboxylated surfaces or hydroxylated surfaces using standard immobilization chemistries. Examples of attachment agents are cyanogen bromide, succinimide, aldehydes, tosyl chloride, avidin-biotin, photocrosslinkable agents, epoxides and maleimides. A preferred attachment agent is the heterobifunctional cross-linker N-[γ-Maleimidobutyryloxy]succinimide ester (GMBS). These and other attachment agents, as well as methods for their use in attachment, are described in *Protein immobilization: fundamentals and applications*, Richard F. Taylor, ed. (M. Dekker, New York, 1991), Johnstone and Thorpe, *Immunochemistry In Practice* (Blackwell Scientific Publications, Oxford, England, 1987) pages 209–216 and 241–242, and *Immobilized Affinity Ligands*, Craig T. Hermanson et al., eds. (Academic Press, New York, 1992). Antibodies can be attached to a substrate by chemically cross-linking a free amino group on the antibody to reactive side groups present within the solid-state substrate. For example, antibodies may be chemically cross-linked to a substrate that contains free amino, carboxyl, or sulfur groups using glutaraldehyde, carbodiimides, or GMBS, respectively, as cross-linker agents. In this method, aqueous solutions containing free antibodies are incubated with the solid-state substrate in the presence of glutaraldehyde or carbodiimide.

A preferred method for attaching antibodies or other proteins to a solid-state substrate is to functionalize the substrate with an amino- or thiol-silane, and then to activate the functionalized substrate with a homobifunctional cross-linker agent such as (Bis-sulfo-succinimidyl suberate ($BS^3$) or a heterobifunctional cross-linker agent such as GMBS. For cross-linking with GMBS, glass substrates are chemically functionalized by immersing in a solution of mercaptopropyltrimethoxysilane (1% vol/vol in 95% ethanol pH 5.5) for 1 hour, rinsing in 95% ethanol and heating at 120° C. for 4 hrs. Thiol-derivatized slides are activated by immersing in a 0.5 mg/ml solution of GMBS in 1% dimethylformamide, 99% ethanol for 1 hour at room temperature. Antibodies or proteins are added directly to the activated substrate, which are then blocked with solutions containing agents such as 2% bovine serum albumin, and air-dried. Other standard immobilization chemistries are known by those of skill in the art.

Each of the components (analyte capture agents, accessory molecules, and/or analytes) immobilized on the solid support preferably is located in a different predefined region of the solid support. Each of the different predefined regions can be physically separated from each other of the different regions. The distance between the different predefined regions of the solid support can be either fixed or variable. For example, in an array, each of the components can be arranged at fixed distances from each other, while components associated with beads will not be in a fixed spatial relationship. In particular, the use of multiple solid support units (for example, multiple beads) will result in variable distances.

Components can be associated or immobilized on a solid support at any density. Components preferably are immobilized to the solid support at a density exceeding 400 different components per cubic centimeter. Arrays of components can have any number of components. For example, an array can have at least 1,000 different components immobilized on the solid support, at least 10,000 different components immobilized on the solid support, at least 100,000 different components immobilized on the solid support, or at least 1,000,000 different components immobilized on the solid support.

L. DNA Polymerases

DNA polymerases useful in the rolling circle replication step of RCA must perform rolling circle replication of primed single-stranded circles. Such polymerases are referred to herein as rolling circle DNA polymerases. For rolling circle replication, it is preferred that a DNA polymerase be capable of displacing the strand complementary to the template strand, termed strand displacement, and lack a 5' to 3' exonuclease activity. Strand displacement is necessary to result in synthesis of multiple tandem copies of an amplification target circle. A 5' to 3' exonuclease activity, if present, might result in the destruction of the synthesized strand. It is also preferred that DNA polymerases for use in the disclosed method are highly processive. The suitability of a DNA polymerase for use in the disclosed method can be readily determined by assessing its ability to carry out rolling circle replication. Preferred rolling circle DNA polymerases are bacteriophage φ29 DNA polymerase (U.S. Pat. Nos. 5,198,543 and 5,001,050 to Blanco et al.), phage M2 DNA polymerase (Matsumoto et al., *Gene* 84:247 (1989)), phage φPRD1 DNA polymerase (Jung et al., *Proc. Natl. Acad. Sci. USA* 84:8287 (1987)), VENT® DNA polymerase (Kong et al., *J. Biol. Chem.* 268:1965–1975 (1993)), Klenow fragment of DNA polymerase I (Jacobsen et al., *Eur. J. Biochem.* 45:623–627 (1974)), T5 DNA polymerase (Chatterjee et al., *Gene* 97:13–19 (1991)), PRD1 DNA polymerase (Zhu and Ito, *Biochim. Biophys. Acta.* 1219:267–276 (1994)), modified T7 DNA polymerase (Tabor and Richardson, *J. Biol. Chem.* 262:15330–15333 (1987); Tabor and Richardson, *J. Biol. Chem.* 264:6447–6458 (1989); Sequenase™ (U.S. Biochemicals)), and T4 DNA polymerase holoenzyme (Kaboord and Benkovic, *Curr. Biol.* 5:149–157 (1995)). φ29 DNA polymerase is most preferred.

Strand displacement can be facilitated through the use of a strand displacement factor, such as helicase. It is considered that any DNA polymerase that can perform rolling circle replication in the presence of a strand displacement factor is suitable for use in the disclosed method, even if the DNA polymerase does not perform rolling circle replication in the absence of such a factor. Strand displacement factors useful in RCA include BMRF1 polymerase accessory subunit (Tsurumi et al., *J. Virology* 67(12):7648–7653 (1993)), adenovirus DNA-binding protein (Zijderveld and van der Vliet, *J. Virology* 68(2):1158–1164 (1994)), herpes simplex viral protein ICP8 (Boehmer and Lehman, *J. Virology* 67(2):711–715 (1993); Skaliter and Lehman, *Proc. Natl. Acad. Sci. USA* 91(22):10665–10669 (1994)), single-stranded DNA binding proteins (SSB; Rigler and Romano, *J. Biol. Chem.* 270:8910–8919 (1995)), and calf thymus helicase (Siegel et al., *J. Biol. Chem.* 267:13629–13635 (1992)).

The ability of a polymerase to carry out rolling circle replication can be determined by using the polymerase in a rolling circle replication assay such as those described in Fire and Xu, *Proc. Natl. Acad. Sci. USA* 92:4641–4645 (1995).

The materials described above can be packaged together in any suitable combination as a kit useful for performing the disclosed method. For example, a kit can include a plurality of reporter binding primers and/or a plurality of analyte capture agents. The analyte capture agents in the kit can be associated with a solid support.

Method

The disclosed method is a form of RCA where a reporter binding primer provides the rolling circle replication primer for amplification of an amplification target circle. The disclosed method allows RCA to produce an amplified signal (that is, tandem sequence DNA (TS-DNA)) based on association of the reporter binding primer with an analyte. The specific primer sequence that is a part of the reporter binding primer provides the link between the specific interaction of the reporter binding primer to an analyte (via the affinity portion of the reporter binding primer) and RCA. For RCA, an amplification target circle (ATC) is hybridized to the rolling circle replication primer sequence of the reporter binding primer, followed by amplification of the ATC by RCA. The resulting TS-DNA incorporates the rolling circle replication primer sequence of the reporter binding primer at one end, thus anchoring the TS-DNA to the site of the analyte. The disclosed method can be performed using any analyte. Preferred analytes are proteins and peptides.

The disclosed method is particularly useful for generating a profile of analytes present in a given sample. For example, the presence and amount of various proteins present in cells can be assessed, thus providing a direct protein expression profile. Such analysis, a form of proteomics, is analogous to genomics analysis of the presence and expression of nucleic acids. Multiple analyte analysis, such as the proteomics mode of the disclosed invention, is preferably carried out using arrays of analyte capture agents. By including in the array an analyte capture agent specific for all of the analytes to be assessed, the full range of analytes can be assayed in a single procedure. This form of the method also allows easy comparison of the same suite of analytes in multiple samples.

In a preferred form of the disclosed method, the analytes in two (or more) different samples can be assessed in the same array by mixing a different set of reporter binding primers with each sample. Each set of reporter binding primers has the same set of specific binding molecules but a different set of rolling circle replication primers. By making the different rolling circle replication primers specific for different amplification target circles, the amplification of a specific amplification target circle will indicate in which sample the corresponding analyte is present.

Identification of multiple analytes can be facilitated by using analyte capture agents to capture and/or separate analytes based on their identity. For example, an array of immobilized analyte capture agents can be used to associate particular analytes with predefined regions of the array. Detection of an analyte in that region identifies the analyte. One useful form of analyte capture agents is peptides. When various peptides are immobilized in an array, they can be used as "bait" for analytes. For example, an array of different peptides can be used to access whether a sample has analytes that interact with any of the peptides. Comparisons of different samples can be made by, for example, noting differences in the peptides to which analytes in the different samples become associated. In another form of the disclosed method, an array of analyte capture agents specific for analytes of interest can be used to access the presence of a whole suite of analytes in a sample.

In another form of the disclosed method, accessory molecules can be used to affect the interaction of analytes with specific binding molecules or analyte capture agents. For example, the disclosed method can be used to screen for competitors (or binding co-factors) of an analyte interaction with a specific binding molecule or analyte capture agent. If an accessory molecule affects interaction of the analyte, the results of RCA will change since the association of the reporter binding primer to the analyte (or of the analyte capture agent to the analyte) will be lost or gained. An example of competition for interaction of an analyte and analyte capture agent is illustrated in FIG. 14.

Different modified forms of analytes can also be detected with the disclosed method. For example, phosphorylated and glycosylated forms of proteins can be detected. This can be accomplished, for example, by using reporter binding primers having specific binding molecules specific for the different forms of analyte.

In another aspect, the disclosed method involves immobilization of analytes present in complex biological samples and determining and quantitating their presence in the samples. The process of identifying and quantitating analytes by immobilization is described herein using samples containing allergens. For example, allergens present in biological extracts and fluids can be identified by first selectively immobilizing them on microarrays as described in Example 8. An immunoRCA microarray assay can then be employed for detection and quantitation.

In another aspect, the disclosed method involves multiplexed detection and quantitation of more than one analytes in a sample. This is illustrated in Example 9 where a microarray containing several test sites, each test site containing an immobilized capture antibody was incubated with sample containing a mixture of protein analytes to be detected. The microarrays were next incubated with a mixture containing at least one biotinylated antibody for each analyte. An immunoRCA microarray assay was then employed for detection and quantitation.

In another aspect, an immunoRCA microarray assay can be performed in 16 microwell-glass slides, wherein each well is separated by a Teflon mask. This is illustrated in Example 8 where microarrays of 100–400 spots were printed in each microwell. Each of these wells was used to assay different samples, and controls. Multiwell slides were also printed with arrays of anti-IgE capture antibodies in 6 of the 16 wells. Semi-automation of immunoRCA assays on allergen microarrays in this multiwell format can be implemented, for example, on an inexpensive Beckman BioMek liquid handling robot.

Microarray-based immunoRCA assay can be applied to other multiplexed antibody assays. For example, certain immunological reactions are caused by specific $IgG_4$ rather than IgE (AAAI Board of Directors, *J. Allergy Clin Immunol.* 95:652–654 (1995)). The use of an anti-human $IgG_4$ conjugated to a DNA primer complementary to a DNA circle that is different in sequence from the DNA circle to which the primer conjugated to an anti-IgE is complementary would allow the simultaneous measurement of allergen-specific $IgG_4$ and IgE. Such an assay can be used during allergen desensitization therapy or for monitoring response to anti-IgE therapy (Chang *Nature Biotech.* 18:157–162 (2000)).

The disclosed method generally includes the following steps:

(a) bringing into contact one or more analyte samples and one or more reporter binding primers, and incubating the analyte samples and the reporter binding primers under conditions that promote interaction of the specific binding molecules and analytes. Each reporter binding primer includes a specific binding molecule and a rolling circle replication primer, and each specific binding molecule interacts with an analyte directly or indirectly.

(b) prior to, simultaneous with, or following step (a), bringing into contact the reporter binding primers and one or more amplification target circles, and incubating the reporter binding primers and amplification target circles under conditions that promote hybridization between the amplification target circles and the rolling circle replication primers. The amplification target circles each comprise a single-stranded, circular DNA molecule including a primer complement portion. The primer complement portion is complementary to at least one of the rolling circle replication primers.

(c) following step (b) and prior to, simultaneous with, or following step (a), incubating the reporter binding primers and amplification target circles under conditions that promote replication of the amplification target circles. Replication of the amplification target circles results in the formation of tandem sequence DNA, and detection of tandem sequence DNA indicates the presence of the corresponding analytes. Preferably, the analytes are separated from the analyte samples prior to, simultaneous with, or following steps (a), (b), or (c).

The method can also include bringing into contact at least one of the analyte samples and one or more analyte capture agents, and separating analyte capture agents from the analyte samples, thus separating analytes from the analyte samples. Each analyte capture agent interacts with an analyte directly or indirectly, and at least one analyte, if present in the analyte sample, interacts with at least one analyte capture agent. The method can also include bringing into contact at least one of the analyte samples and at least one of the reporter binding primers with at least one accessory molecule. The accessory molecule affects the interaction of at least one of the analytes and at least one of the specific binding molecules or at least one of the analyte capture agents.

The method can also include, following step (a) and prior to bringing the analyte samples and the solid support into contact, mixing one or more of the first analyte samples and one or more of the second analyte samples. In this form of the method, the analyte samples include one or more first analyte samples and one or more second analyte samples, and the reporter binding primers include one or more first reporter binding primers and one or more second reporter binding primers. For each first reporter binding primer there is a matching second reporter binding primer, and the specific binding molecules of the first reporter binding primers interacts with the same analyte as the specific binding molecules of the matching second reporter binding primer. Also, the rolling circle replication primer of each different reporter binding primer is different, each different rolling circle replication primer primes replication of a different one of the amplification target circles, and each different amplification target circle produces a different tandem sequence DNA. The presence or absence of the same analyte in different analyte samples is indicated by the presence or absence of corresponding tandem sequence DNA.

Another form of the method includes, prior to, simultaneous with, or following step (a), bringing into contact one or more first analyte capture agents and one or more first analyte samples, and bringing into contact one or more second analyte capture agents and one or more second analyte samples. Each analyte capture agent includes an analyte interaction portion and a capture portion. For each first analyte capture agent there is a matching second analyte capture agent. The analyte interaction portions of the first analyte capture agents interact with the same analyte as the analyte interaction portions of the matching second analyte capture agents. The capture portions of the first and second analyte capture agents each interact with a specific binding molecule of one or more of the reporter binding primers, and the capture portions of the first analyte capture agents interact with different specific binding molecules than the capture portions of the matching second analyte capture agents. Each different specific binding molecule is part of a different one of the reporter binding primers. The rolling circle replication primer of each different reporter binding primer is different, each different rolling circle replication primer primes replication of a different one of the amplification target circles, and each different amplification target circle produces a different tandem sequence DNA. The presence or absence of the same analyte in different analyte samples is indicated by the presence or absence of corresponding tandem sequence DNA.

The method can also be performed where at least one of the analytes is a modified form of another analyte, the specific binding molecule of at least one of the reporter binding primers interacts, directly or indirectly, with the analyte that is a modified form of the other analyte, and the specific binding molecule of another reporter binding primer interacts, directly or indirectly, with the other analyte.

Another form of the disclosed method generally includes the following steps:

(a) bringing into contact one or more analyte samples and one or more analyte capture agents, and incubating the analyte samples and the analyte capture agents under conditions that promote interaction of the analyte capture agents and analytes. Each analyte capture agent interacts with an analyte directly or indirectly, and at least one analyte, if present in the analyte sample, interacts with at least one analyte capture agent.

(b) prior to, simultaneous with, or following step (a), bringing into contact at least one of the analyte samples and one or more reporter binding primers, and incubating the analyte samples and the reporter binding primers under conditions that promote interaction of the specific binding molecules and analyte capture agents. Each reporter binding primer comprises a specific binding molecule and a rolling circle replication primer, and each specific binding molecule interacts with an analyte capture agent directly or indirectly.

(c) prior to, simultaneous with, or following steps (a) or (b), bringing into contact the reporter binding primers and one or more amplification target circles, and incubating the reporter binding primers and amplification target circles under conditions that promote hybridization between the amplification target circles and the rolling circle replication primers. The amplification target circles each comprise a single-stranded, circular DNA molecule comprising a primer complement portion, and the primer complement portion is complementary to at least one of the rolling circle replication primers.

(d) following step (c) and prior to, simultaneous with, or following steps (a) or (b), incubating the reporter binding primers and amplification target circles under conditions that promote replication of the amplification target circles. Replication of the amplification target circles results in the formation of tandem sequence DNA, and detection of tandem sequence DNA indicates the presence of the corresponding analytes.

Another form of the disclosed method generally includes the following steps:

(a) treating one or more analyte samples so that one or more analytes are modified.

(b) bringing into contact at least one of the analyte samples and one or more reporter binding primers, and incubating the analyte samples and the reporter binding primers under conditions that promote interaction of the specific binding molecules and modified analytes. Each reporter binding primer comprises a specific binding molecule and a rolling circle replication primer, and each specific binding molecule interacts with a modified analyte directly or indirectly.

(c) prior to, simultaneous with, or following steps (a) or (b), bringing into contact the reporter binding primers and one or more amplification target circles, and incubating the reporter binding primers and amplification target circles under conditions that promote hybridization between the amplification target circles and the rolling circle replication primers. The amplification target circles each comprise a single-stranded, circular DNA molecule comprising a primer complement portion, and the primer complement portion is complementary to at least one of the rolling circle replication primers.

(d) following step (c) and prior to, simultaneous with, or following steps (a) or (b), incubating the reporter binding primers and amplification target circles under conditions that promote replication of the amplification target circles. Replication of the amplification target circles results in the formation of tandem sequence DNA, and detection of tandem sequence DNA indicates the presence of the corresponding analytes.

Another form of the disclosed method generally includes the following steps:

(a) bringing into contact one or more analyte samples and one or more arrays. Each array comprises a set of analyte capture agents, a set of accessory molecules, or both, and each analyte capture agent interacts with an analyte directly or indirectly.

(b) prior to, simultaneous with, or following step (a), bringing into contact at least one of the analyte samples and one or more reporter binding primers. Each reporter binding primer comprises a specific binding molecule and a rolling circle replication primer, each specific binding molecule interacts with an analyte directly or indirectly, and each accessory molecule affects the interaction of at least one of the analytes and at least one of the specific binding molecules or at least one of the analyte capture agents.

(c) simultaneous with, or following, either or both steps (a) and (b), incubating the analyte samples, the arrays, and the reporter binding primers under conditions that promote interaction of the specific binding molecules, analytes, analyte capture agents, and accessory molecules.

(d) prior to, simultaneous with, or following step (b), bringing into contact the reporter binding primers and one or more amplification target circles, and incubating the reporter binding primers and amplification target circles under conditions that promote hybridization between the amplification target circles and the rolling circle replication primers. The amplification target circles each comprise a single-stranded, circular DNA molecule comprising a primer complement portion, and the primer complement portion is complementary to at least one of the rolling circle replication primers.

(e) following step (d) and prior to, simultaneous with, or following steps (a), (b), or (c), incubating the reporter binding primers and amplification target circles under conditions that promote replication of the amplification target circles. Replication of the amplification target circles results in the formation of tandem sequence DNA, and detection of tandem sequence DNA indicates the presence of the corresponding analytes.

The amplification target circles serve as substrates for a rolling circle replication. This reaction requires the addition of two reagents: (a) a rolling circle replication primer, which is complementary to the primer complement portion of the ATC, and (b) a rolling circle DNA polymerase. The DNA polymerase catalyzes primer extension and strand displacement in a processive rolling circle polymerization reaction that proceeds as long as desired, generating a molecule of up to 100,000 nucleotides or larger that contains up to approximately 1000 tandem copies of a sequence complementary to the amplification target circle. A preferred rolling circle DNA polymerase is the DNA polymerase of the bacteriophage φ29.

Many different forms of RCA can be used in the disclosed method, most of which are described in U.S. Pat. No. 5,854,033 and WO 97/19193. For example, linear rolling circle amplification (LRCA) involves the basic rolling circle replication of an amplification target circle to form a strand of TS-DNA. Exponential rolling circle amplification (ERCA) involves replication of TS-DNA by strand displacement replication initiated at the numerous repeated sequences in the TS-DNA. Multiple priming on both strands of TS-DNA leads to an exponential amplification of sequences in the amplification target circle. If desired, the TS-DNA can be collapsed into a compact structure for detection as described in WO 97/19193.

During rolling circle replication one may additionally include radioactive or modified nucleotides such as bromodeoxyuridine triphosphate, in order to label the DNA generated in the reaction. Alternatively, one may include suitable precursors that provide a binding moiety such as biotinylated nucleotides (Langer et al. (1981)).

Examples of proteins that can be analyzed and detected using the disclosed method include IL-1alpha, IL-1beta, IL-1RA, IL-2, IL-3, IL-4, IL-6, IL-6R, IL-7, IL-8, IL-9, IL-10, GROalpha, MIP-1alpha, MIP-1beta, MCP, RANTES, MIF, G-CSF, GM-CSF, M-CSF, EGF, FGF acidic, FGF basic, IGF-1, IGF-2, IFN-gamma, TGF-beta, TNF-alpha, TNF-beta, TNF-RI, TNF-RII, ICAM-1, ICAM-2, IL-2Ra, IL-4R, IL-5, IL-11, IL-12, IL-13, IL-15, IL-16, IL-17, IL-18, IP-10, FGF-4, FGF-6, MCP-2, and MCP-3.

A. Detection of Amplification Products

Current detection technology makes a second cycle of RCA unnecessary in many cases. Thus, one may proceed to detect the products of the first cycle of RCA directly. Detection may be accomplished by primary labeling or by secondary labeling, as described below.

1. Primary Labeling

Primary labeling consists of incorporating labeled moieties, such as fluorescent nucleotides, biotinylated nucleotides, digoxygenin-containing nucleotides, or bromodeoxyuridine, during rolling circle replication in RCA. For example, one may incorporate cyanine dye UTP analogs (Yu et al. (1994) at a frequency of 4 analogs for every 100 nucleotides. A preferred method for detecting nucleic acid amplified in situ is to label the DNA during amplification with BrdUrd, followed by binding of the incorporated BUDR with a biotinylated anti-BUDR antibody (Zymed Labs, San Francisco, Calif.), followed by binding of the biotin moieties with Streptavidin-Peroxidase (Life Sciences, Inc.), and finally development of fluorescence with Fluorescein-tyramide (DuPont de Nemours & Co., Medical Products Dept.).

2. Secondary Labeling with Detection Probes

Secondary labeling consists of using suitable molecular probes, referred to as detection probes, to detect the amplified DNA or RNA. For example, an amplification target circle may be designed to contain several repeats of a known arbitrary sequence, referred to as detection tags. A secondary hybridization step can be used to bind detection probes to these detection tags. The detection probes may be labeled as described above with, for example, an enzyme, fluorescent moieties, or radioactive isotopes. By using three detection tags per amplification target circle, and four fluorescent moieties per each detection probe, one may obtain up to twelve fluorescent signals for every amplification target circle repeat in the TS-DNA, yielding up to 12,000 fluorescent moieties for every amplification target circle that is amplified by RCA.

3. Multiplexing and Hybridization Array Detection

RCA is easily multiplexed by using sets of different amplification target circles, each set carrying different target probe sequences designed for binding to unique targets. Note that although the target probe sequences designed for each target are different, the primer complement portion may remain unchanged, and thus the primer for rolling circle replication can remain the same for all targets. The TS-DNA molecules generated by RCA are of high molecular weight and low complexity; the complexity being the length of the amplification target circle. There are two alternatives for capturing a given TS-DNA to a fixed position in a solid support. One is to include within the spacer region of the amplification target circles a unique address tag sequence for each unique amplification target circle. TS-DNA generated from a given amplification target circle will then contain sequences corresponding to a specific address tag sequence. A second and preferred alternative is to use the target sequence present on the TS-DNA as the address tag.

4. Combinatorial Multicolor Coding

A preferred form of multiplex detection involves the use of a combination of labels that either fluoresce at different wavelengths or are colored differently. One of the advantages of fluorescence for the detection of hybridization probes is that several targets can be visualized simultaneously in the same sample. Using a combinatorial strategy, many more targets can be discriminated than the number of spectrally resolvable fluorophores. Combinatorial labeling provides the simplest way to label probes in a multiplex fashion since a probe fluor is either completely absent (−) or present in unit amounts (+); image analysis is thus more amenable to automation, and a number of experimental artifacts, such as differential photobleaching of the fluors and the effects of changing excitation source power spectrum, are avoided.

The combinations of labels establish a code for identifying different detection probes and, by extension, different analytes to which those detection probes are associated with. This labeling scheme is referred to as Combinatorial Multicolor Coding (CMC). Such coding is described by Speicher et al., *Nature Genetics* 12:368–375 (1996). Any number of labels, which when combined can be separately detected, can be used for combinatorial multicolor coding. It is preferred that 2, 3, 4, 5, or 6 labels be used in combination. It is most preferred that 6 labels be used. The number of labels used establishes the number of unique label combinations that can be formed according to the formula $2^N-1$, where N is the number of labels. According to this formula, 2 labels forms three label combinations, 3 labels forms seven label combinations, 4 labels forms 15 label combinations, 5 labels form 31 label combinations, and 6 labels forms 63 label combinations.

Speicher et al. describes a set of fluors and corresponding optical filters spaced across the spectral interval 350–770 nm that give a high degree of discrimination between all possible fluor pairs. This fluor set, which is preferred for combinatorial multicolor coding, consists of 4'-6-diamidino-2-phenylinodole (DAPI), fluorescein (FITC), and the cyanine dyes Cy3, Cy3.5, Cy5, Cy5.5 and Cy7. Any subset of this preferred set can also be used where fewer combinations are required. The absorption and emission maxima, respectively, for these fluors are: DAPI (350 nm; 456 mm), FITC (490 nm; 520 nm), Cy3 (554 nm; 568 nm), Cy3.5 (581 nm; 588 mm), Cy5 (652 nm; 672 mm), Cy5.5 (682 nm; 703 nm) and Cy7 (755 nm; 778 nm). The excitation and emission spectra, extinction coefficients and quantum yield of these fluors are described by Ernst et al., *Cytometry* 10:3–10 (1989), Mujumdar et al., *Cytometry* 10:11–19 (1989), Yu, *Nucleic Acids Res.* 22:3226–3232 (1994), and Waggoner, *Meth. Enzymology* 246:362–373 (1995). These fluors can all be excited with a 75W Xenon arc.

B. Further Amplification

Secondary DNA strand displacement is another way to amplify TS-DNA. Secondary DNA strand displacement is accomplished by hybridizing secondary DNA strand displacement primers to TS-DNA and allowing a DNA polymerase to synthesize DNA from these primed sites. The product of secondary DNA strand displacement is referred to as secondary tandem sequence DNA or TS-DNA-2. Secondary DNA strand displacement and strand displacement cascade amplification are described in U.S. Pat. No. 5,854,033 and WO 97/19193.

EXAMPLES

A. Example 1

This example demonstrates the construction and characterization of antibody-DNA conjugates that are used as Reporter Binding Primers.

Oligonucleotides. All oligonucleotides used were synthesized on a Perseptive Biosystems Expedite DNA Synthesizer and purified by reverse-phase HPLC. Circle DNAs were constructed as previously described (4). Conjugate Rolling Circle Replication primer: 5' Thiol-GTA CCA TCA TAT ATG TCC GTG CTA GAA GGA AAC AGT TAC A-3' (SEQ ID NO:1); Amplification Target Circle DNA: 5'-TAG CAC GGA CAT ATA TGA TGG TAC CGC AGT ATG AGT ATC TCC TAT CAC TAC TAA GTG GAA GAA ATG TAA CTG TTT CCT TC-3' (SEQ ID NO:2); Detection Probes-5' Cy3 TAT ATG ATG GTA CCG CAG Cy3 3' (SEQ ID NO:3), 5' Cy3 TGA GTA TCT CCT ATG ACT Cy3 3' (SEQ ID NO:4), 5' Cy3 TAA GTG GAA GAA ATG TAA Cy3 3' (SEQ ID NO:5).

Figure 2:
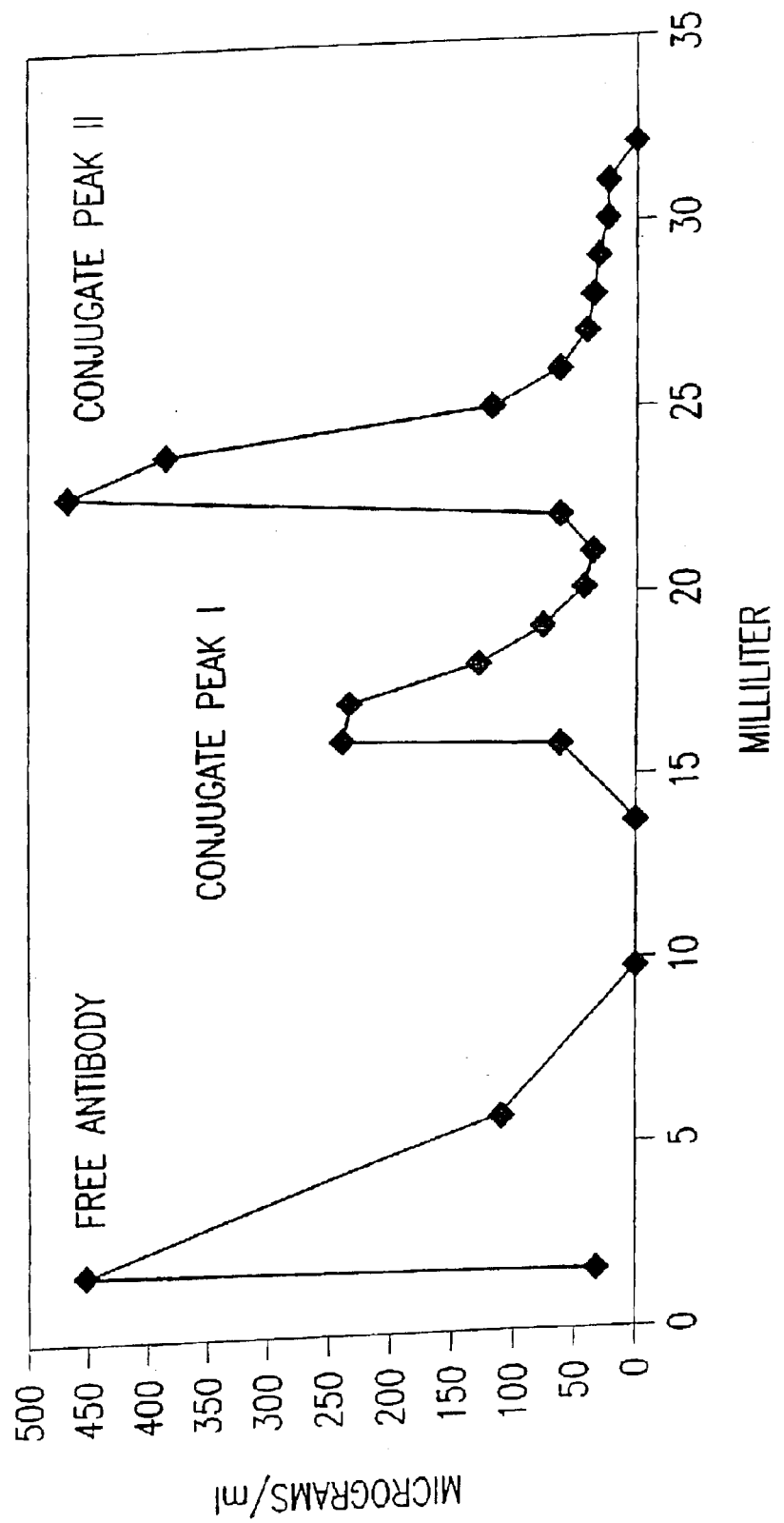
FIG. 2 is a graph of protein (in micrograms/ml) versus column fractions. Conjugation mixtures were loaded onto an anion exchange column and eluted with a salt gradient as described in Example 1. Fractions were collected and assayed for protein content. Protein peaks were pooled and assayed for antibody/DNA content by UV spectroscopy and SDS-PAGE.
Figure 3:
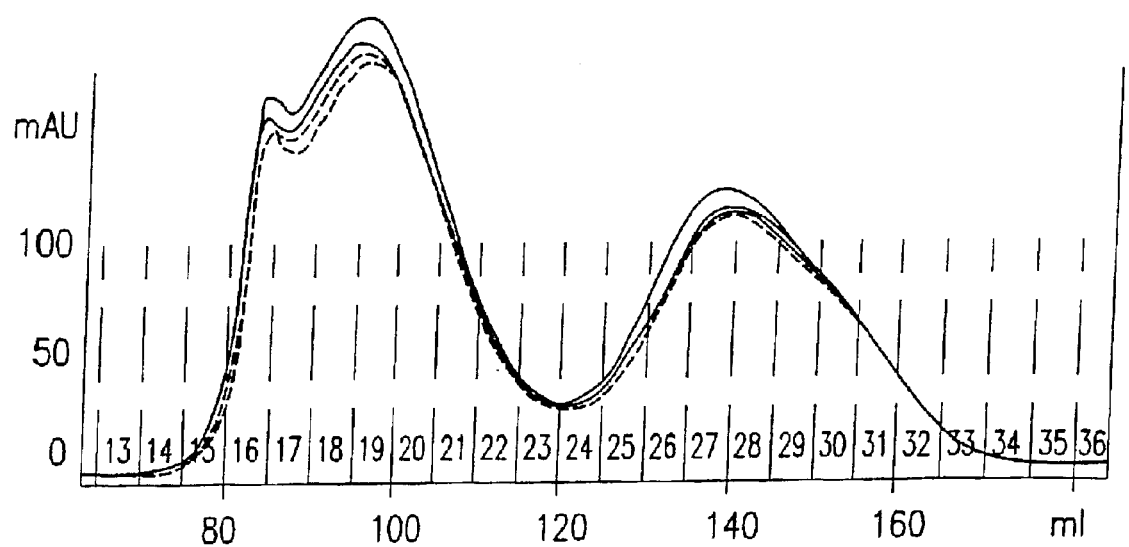
FIG. 3 is a graph of absorbance (in absorbance units$\times 10^{-3}$ at 260 nm) versus column fractions. Fractions from the anion exchange chromatography containing antibody-DNA conjugate were pooled, concentrated, and loaded onto a size exclusion column as described in Example 1. Elution of DNA in sodium phosphate pH 7.5, 150 mM NaCl, 1 mM EDTA, 0.01% Tween 20 was followed at 260 nm. The graph shows overlays of multiple load/elution runs; fractions 16–20 were pooled and checked for purity.

Antibody-DNA conjugation. Antibody was buffer-exchanged into 50 mM NaPhosphate pH 7.5, 150 mM NaCl, 1 mM EDTA by chromatography over a PD-10 column (Amersham-Pharmacia Biotech). Desalted antibody (41 nmoles) was treated with a 10-fold molar excess of sulfo-GMBS (Pierce) under nitrogen in the dark for 30 min. at 37° C., followed by 30 min. at room temperature. Unreacted sulfo-GMBS was removed by chromatography over a PD-10 column equilibrated with NaPhosphate pH 7.5, 150 mM NaCl. The antibody was then concentrated in a Centricon YM-30 at 4° C. The number of maleimides per antibody was determined by utilizing Ellman's reagent (Pierce) to measure sulfhydryls following titration of beta-mercaptoethanol by the activated antibody. 28.1 nmoles of sulfo-GMBS activated antibody and 142 nmoles of 5' thiol oligonucleotide were conjugated in a volume of 825 microliters for two hours at room temperature, followed by overnight at 4° C. Antibody conjugated to oligonucleotide was purified by anion exchange chromatography on Q-Sepharose (Amersham Pharmacia Biotech) using a salt gradient (FIG. 2). Fractions containing conjugate were pooled and subjected to size exclusion chromatography on Superdex-200 (Pharmacia) at 4° C. to remove free oligonucleotide (FIG. 3).

Figure 4:
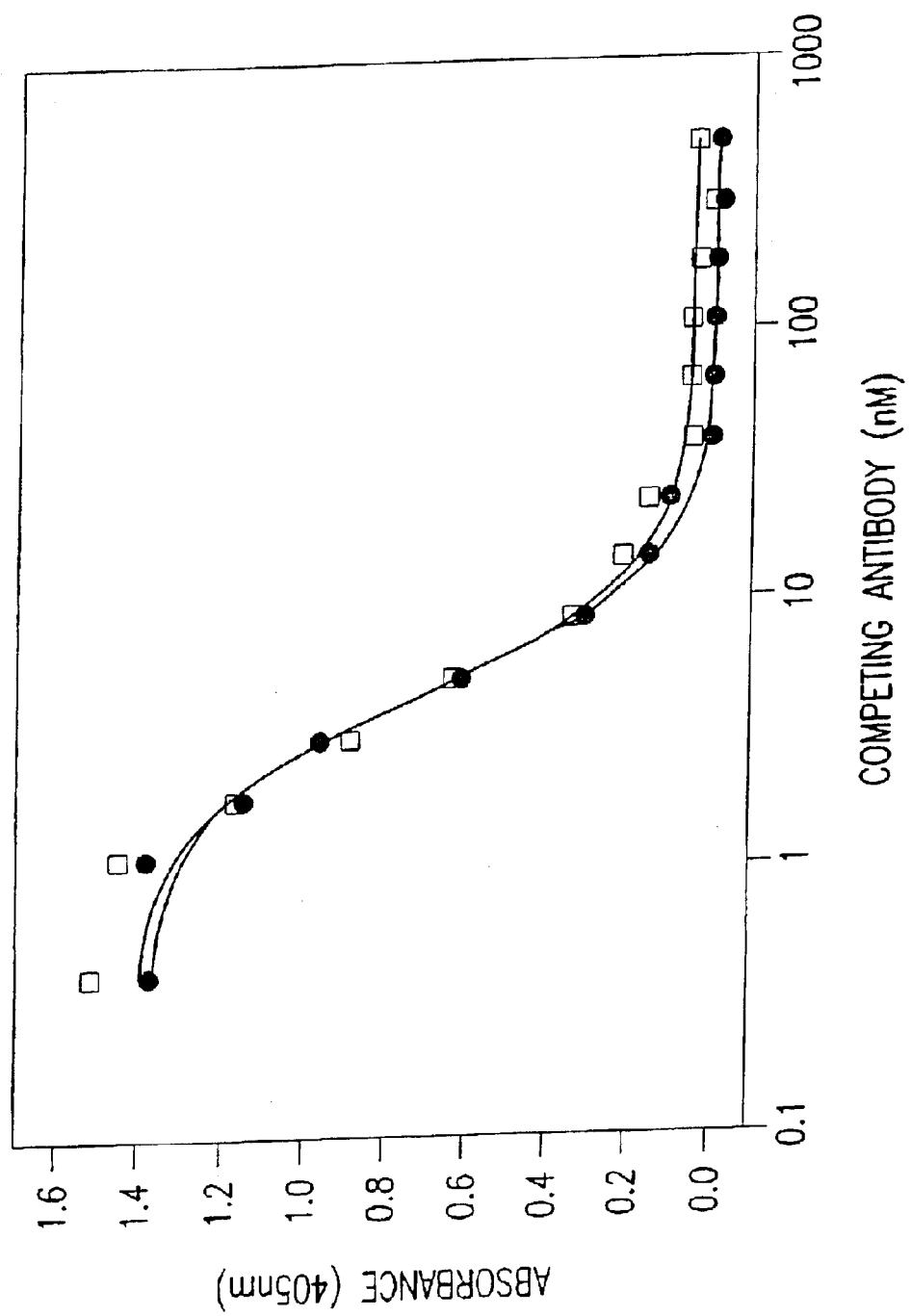
FIG. 4 is a graph of absorbance (at 405 nm) versus competing antibody concentration (in nM). The graph shows the effect of conjugation on the avidity of an anti-human IgE monoclonal antibody. Competitive ELISA assays were carried out as described in Example 1 with the anti-human IgE antibody in the DNA-conjugated (open squares) or unconjugated (filled circles) forms.

Competitive ELISA assays were carried out to assess the ability of the conjugate to bind cognate antigen. In these assays, the matching unconjugated and DNA-conjugated antibodies were assessed in parallel for their ability to compete with a reporter antibody for binding to antigen. Briefly: Multiwell plates (Nunc Maxisorp) were coated with capture antibody (BiosPacific goat polyclonal anti-IgE) at 2 microg/ml in 0.1 M $NaCO_3$ overnight at 37° C. The antibody solution was replaced with a background blocking solution (5% nonfat dry milk/0.05% $NaN_3$ in TBS), and incubated for 1 hour at 37° C. Blocker was removed with 4 washes of TBS/0.05% Tween 20 and purified human IgE (from Fitzgerald multiple myeloma cells) was added at 500 ng/ml in TBS with incubation for 30 min. at 37° C. IgE was removed with 4 washes of TBS/0.05% Tween 20, followed by addition of pre-made anti-IgE mixtures consisting of competitor (unconjugated anti-IgE or DNA–anti-IgE conjugate) and reporter (biotinylated anti-IgE, PharMingen). The biotinylated anti-IgE was held at a fixed level while the competitor anti-IgE was present at various levels. The anti-IgE mixtures were incubated in the wells for 30 min. at 37° C. Following 3 washes of TBS/0.05% Tween 20, remaining biotinylated anti-IgE was detected by incubation with NeutrAvidin-alkaline phosphatase (Pierce Chemical Co.) for 30 min. at 37° C. The wells were then washed 3 times with TBS/0.05% Tween 20 and incubated with alkaline phosphatase substrate (p-Nitrophenyl phosphate kit, Pierce Chemical Co.). The color reaction was allowed to develop for 15 min. and absorbance at 405 nm was read in a BioMek FL600 plate reader. The conjugated antibodies, each coupled to about 3 oligonucleotides per mole of protein, exhibited nearly equivalent avidity for antigen as the unconjugated forms (FIG. 4).

Figure 5:
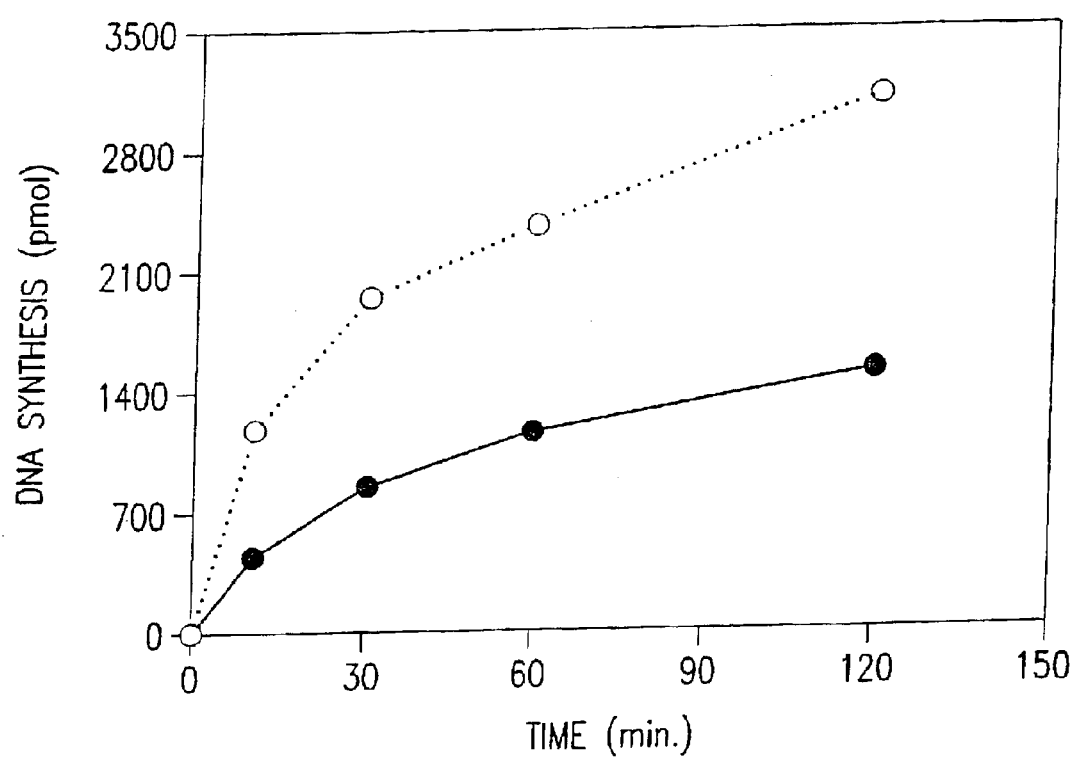
FIG. 5 is a graph of DNA synthesis (in pmoles) versus time. The graph compares free and antibody-conjugated primers in an RCA reaction. RCA with equimolar amounts of anti-human IgE—primer 2 conjugate (open circles) or unconjugated primer 2 was carried out as described in Example 1.

RCA reactions were carried out to assess the ability of the conjugate to serve as a primer. RCA reactions contained 5 nM primer or primer-conjugated antibody, 10 nM circle, 200 ng of *E. coli* SSB (Promega), 0.125 unit of T7 polymerase (USB), 0.4 mM each dATP, dTTP, dGTP, and 0.4 mM [$\alpha$-$^{32}$P] TTP (300–600 cpm/pmol) in 25 $\mu$l of a buffer (pH 7.9) containing 20 mM Tris-acetate, 10 mM magnesium acetate, 50 mM potassium acetate, and 1 mM DTT. Additions were performed on ice and then shifted to 37° C. RCA products at indicated time were quantitated by spotting onto DE81 filters. Antibody-primer conjugate gave more RCA reaction product than an equimolar amount of unconjugated primer in the presence of a complementary circle DNA (FIG. 5), consistent with the observation that each antibody is conjugated to more than one primer. Neither form of primer gave an appreciable product in the absence of complementary circle or in the presence of a non-complementary circle.

B. Example 2

This example demonstrates the use of a Reporter Antibody Primer/Antibody-DNA conjugate for detection of an analyte in an ELISA format. Detection by ImmunoRCA is shown to have superior sensitivity and dynamic range when compared to detection using a conventional antibody-enzyme conjugate.

Figure 6:
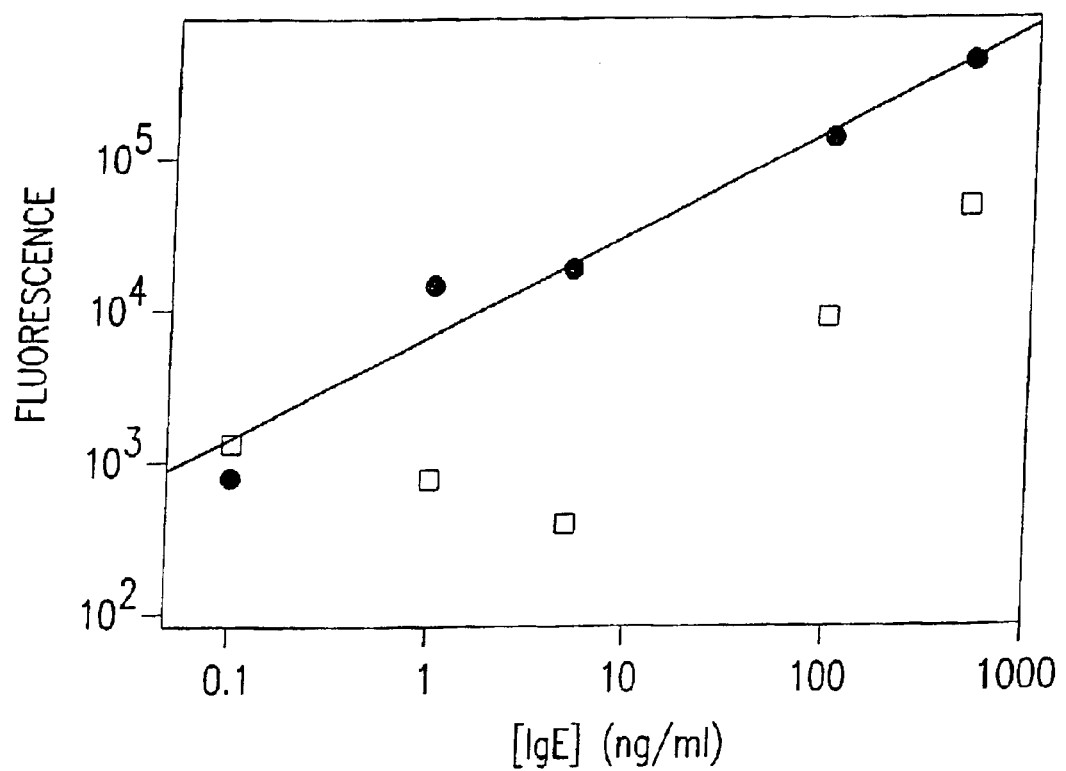
FIG. 6 is a graph of fluorescence versus IgE concentration (in ng/ml). The graph compares immunoRCA and conventional immunoassay in an ELISA format as described in Example 2. Filled circles are ELISA assay of human IgE with immunoRCA, using an anti-human IgE-DNA conjugate. Open squares are ELISA assay of human IgE with an anti-human IgE-alkaline phosphatase conjugate.

ELISA assay. Ninety-six well plates (Nunc Maxisorb) were incubated with 100 µl 2 µg/ml goat polyclonal anti-human IgE per well for 2 hours at 37° C. and then overnight at 4° C. Plates were washed three times with 100 µl TBS/0.05% Tween 20, and then blocked with 5% non-fat dry milk for 2 hours at 37° C. Plates were washed again with TBS/0.05% Tween 20, followed by addition of the IgE analyte at variable concentrations in a 100 µl volume. After a 37° C. incubation for 30 min., plates were washed three times with 100 µl TBS/0.05% Tween 20. In the conventional ELISA assays, anti-human IgE-alkaline phosphatase conjugate was added to each well, and incubated at 37° C. for 30 min. After plates were washed with TBS/0.05% Tween 20, the alkaline phosphatase substrate MUP was added, and fluorescence levels were read after 20 min. on a BioMek FL600 plate reader at an excitation wavelength of 360 nm and an emission wavelength of 460 nm. In the immunoRCA procedures, anti-human IgE-DNA conjugate (5 ng/µl) was added to each well in a 60 µl volume, and incubated at 37° C. for 30 min. After plates were washed three times with 100 µl TBS/0.05% Tween 20, Circle 2 DNA (170 nM) in 60 µl φ29 buffer (250 mM Tris-HCl, pH 7.5, 50 mM MgCl$_2$, 1 mg/ml BSA, 1 mM dATP, dCTP, dGTP, 0.75 mM dTTP, 0.25 mM FITC-12-dUTP) was added to each well, and incubated at 37° C. for 30 min. RCA reactions were initiated by addition of 1.5 µl φ29 DNA polymerase (0.4 U/µl), and continued for 30 min. at 37° C. RCA products were detected by addition of an anti-FITC-alkaline phosphatase conjugate. After a 37° C. incubation for 30 min., plates were washed three times with 100 µl TBS/0.05% Tween 20, MUP substrate was added, and fluorescence levels were read after 20 min. As shown in FIG. 6, the immunoRCA assays gave a dose-response over a greater range of IgE concentration than the conventional assay. In addition, the immunoRCA assay, even in its less amplified linear mode, could detect IgE levels approximately two orders of magnitude lower than those detected by the conventional ELISA assay.

C. Example 3

Figure 7:
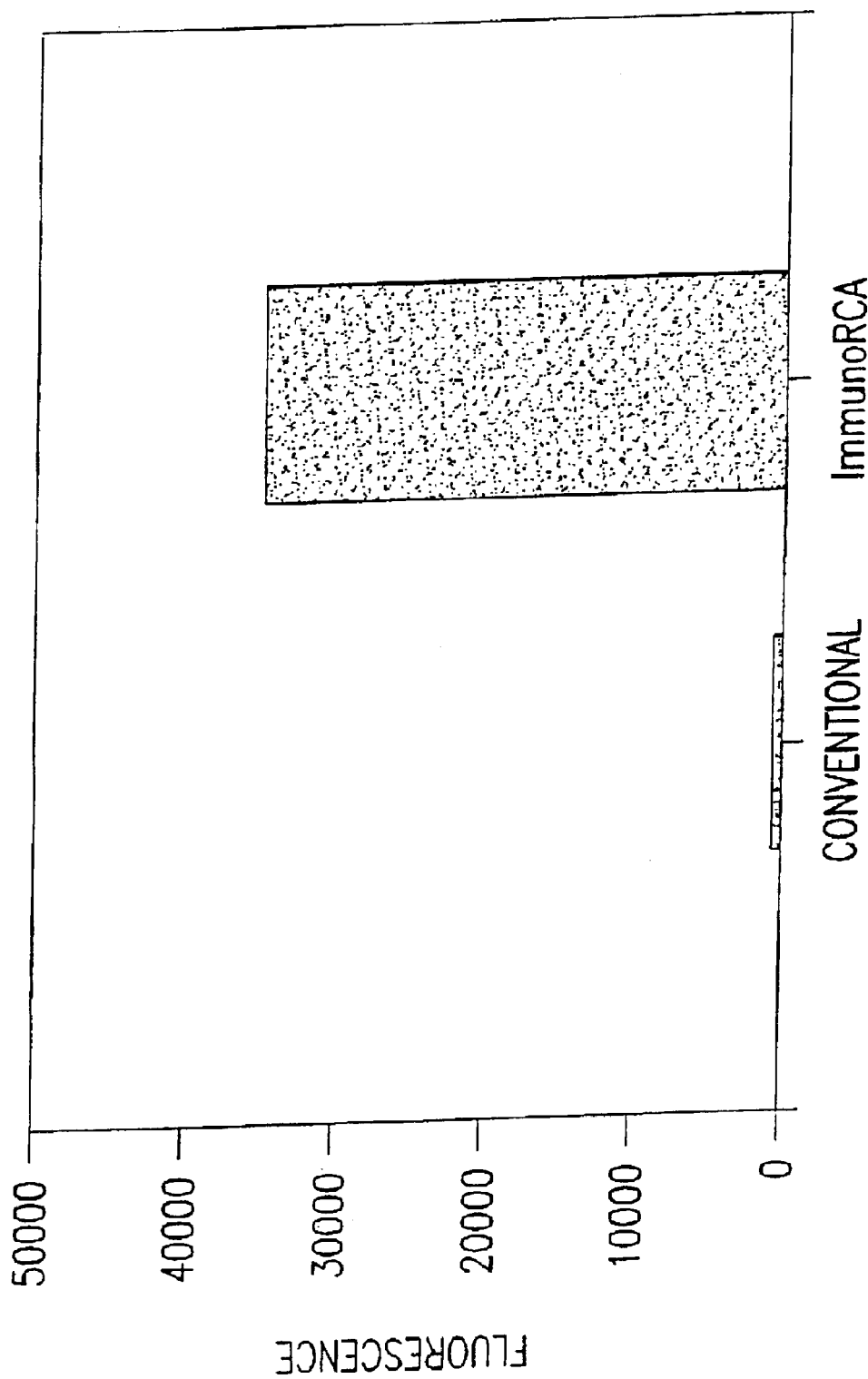
FIG. 7 is a bar graph of fluorescence seen in immunoRCA and conventional immunoassays in a magnetic microparticle format. These assays were carried out using the same anti-human IgE conjugates as those in FIG. 6, except that magnetic microparticles were used as the solid-phase as described in Example 3.

This example demonstrates the use of a Reporter Antibody Primer/Antibody-DNA conjugate for detection of an analyte in a microparticle format. Human IgE was again selected as the test analyte, but this sandwich assay was performed using avidin-coated magnetic microparticles and biotinylated polyclonal anti-human IgE capture antibodies. Briefly, streptavidin-coated magnetic beads (Bangs Laboratories) were coated with a solution of 16 µg/ml biotinylated polyclonal anti-human IgE (Pharmingen) in TBS, washed three times in TBS/0.05% Tween 20, and blocked overnight with 2 mg/ml BSA. Beads were incubated with human IgE (25 ng/ml) in TBS for 20 min. at room temperature, and washed three times in TBS/0.05% Tween 20. Detection of IgE using a conventional anti-IgE-alkaline phosphatase conjugate or an immunoRCA conjugate was carried out as described above for the ELISA assay. In FIG. 7, it can be seen that immunoRCA with the anti-IgE-DNA conjugate gave a strong signal with a moderate concentration of IgE bound to the microparticles. Detection with an anti-IgE-alkaline phosphatase conjugate gave approximately 75-fold less signal than the immunoRCA assay with the same amount of input IgE (25 ng IgE/ml).

D. Example 4

This example demonstrates the suitability of immunoRCA for solid-phase detection on a microspot using detection of prostate specific antigen (PSA) as a model system. For this application, immunoRCA was configured in an indirect sandwich assay format. A mouse monoclonal anti-PSA antibody was used to form the second part of the immuno-sandwich complex. This complex was detected with a polyclonal rabbit anti-mouse IgG antibody that had been conjugated to an oligonucleotide containing a sequence for priming an RCA reaction.

Preparation of microspots. Clean glass slides were chemically functionalized by immersing in a solution of mercaptopropyltrimethoxysilane (1% vol/vol in 95% ethanol pH 5.5 for 1 hour. Slides were rinsed in 95% ethanol for 2 min., dried under nitrogen, and heated at 120° C. for 4 hrs to cure. Thiol-derivatized slides were activated by immersing in a 0.5 mg/ml solution of the heterobifunctional crosslinker sulfo-GMBS (Pierce) in 1% dimethylformamide, 99% ethanol for 1 hour at room temperature. Slides were rinsed with ethanol, dried under nitrogen, and stored in a vacuum dessicator until use. Spotting of Goat anti-PSA polyclonal antibody (BioSpacifics) onto the slides was accomplished by pipetting 0.2 µl of 0.5 mg/ml solution in a grid pattern. Hand-spotted arrays were blocked with 2% BSA (Protease free), air-dried, and stored under nitrogen at 4° C. until use. Immediately prior to use, arrays were rehydrated in 50 ml PBS for 2 min. at room temperature.

Antigen capture. Purified human PSA (BioSpacifics) was diluted in PBS to the desired concentration. Ten µl of the PSA dilution was spotted onto a coverslip (Hybrislip, Grace) that was then inverted onto the slide over the area of the array. The slide was incubated at 37° C. for 30 min. in a humidified chamber, washed twice for 2 min. in PBS/0.05% Tween 20, and tapped dry. Ten µl of a 1:5,000 dilution in PBS of monoclonal anti-PSA antibody was added to the array. The slide was incubated at 37° C. for 30 min. in a humidified chamber, washed twice for 2 min. in PBS/0.05% Tween 20, and tapped dry. Finally, rabbit anti-mouse IgG-DNA conjugate (10 ng/µl in PBS) was added to the array, and incubated at 37° C. for 30 min. in a humidified chamber. Slides were washed twice for 2 min. in PBS/0.05% Tween 20, and tapped dry.

Figure 8:
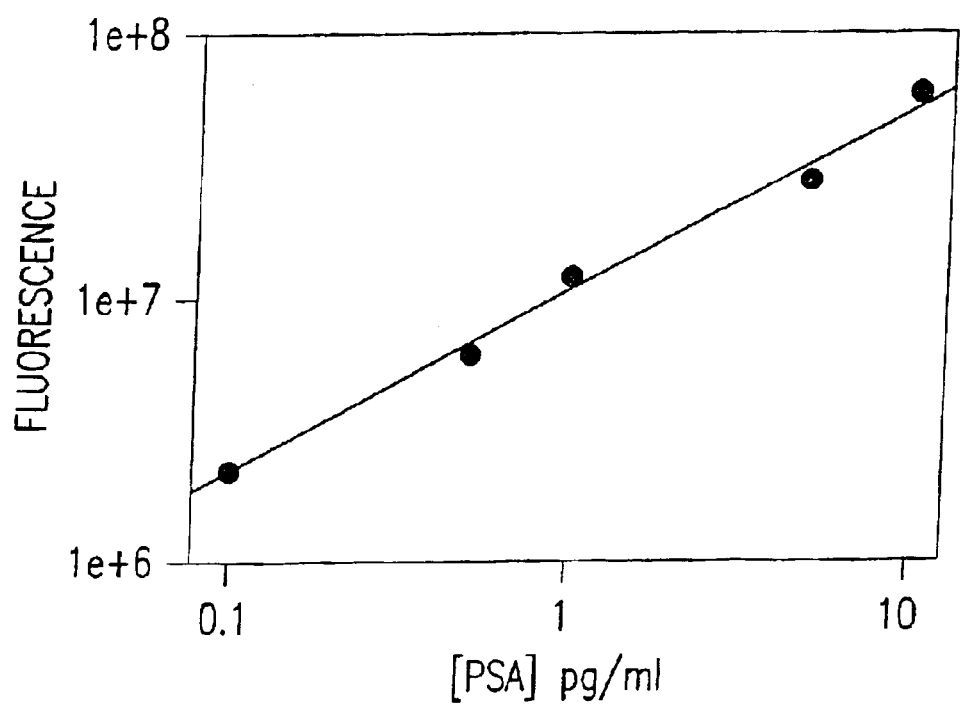
FIG. 8 is a graph of fluorescence versus PSA concentration (in ng/ml). The graph shows detection of PSA by immunoRCA in a microspot assay. Fluorescence in microscope images was quantitated as described in Example 4 and plotted versus PSA concentrations incubated on microspots.

RCA reaction. Circle 1 DNA (200 nM) in 10 µl φ29 buffer (250 mM Tris-HCl, pH 7.5, 50 mM MgCl$_2$, and 1 mg/ml BSA) was added to the array, and incubated at 45° C. for 30 min. Ten µl of RCA reaction mixture (2 mM dATP, dCTP, dGTP, 1.5 mM dTTP, 0.5 mM biotin-16-dUTP dNTPs, φ29 Buffer, 0.4 U/µl φ29 Polymerase) was added to the array and incubated at 37° C. for 30 min. The slide was washed twice for 2 min. at 37° C. in 2×SSC/0.05% Tween 20, twice for 2 min. at room temperature in 2×SSC/0.05% Tween 20 and tapped dry. Ten microliters detector oligo mixture in 2×SSC, 0.05% Tween 20 was added to the array and incubated at 37° C. for 30 min. The slide was washed 4 times for 1 min. in 2×SSC, 0.1% Tween 20. Ten µl of CACHET solution (1 mg/ml Neutravidin, 2×SSC, 0.1% Tween 20, 0.5 mg/ml BSA, 0.5 mg/ml sonicated herring sperm DNA) was added to the array and incubated at 37° C. for 15 min. The slide was washed in 2×SSC, 0.05% Tween 20 for 5 min. with agitation at room temperature, followed by a wash in 2×SSC. Slides were dried under nitrogen and the array portion of the slide was covered with Prolong Antifade (Molecular Probes). Fluorescent imaging was done on a Zeiss epifluorescence microscope equipped with a CCD imaging system and a 100× objective. Fluorescence quantitation was performed using IPLab software. Quantitation of the fluorescence with a CCD-camera equipped microscope indicated that the signal was linear over at least 2 logs of PSA concentration (FIG. 8) and that as little as 0.1 pg/ml PSA (300 zeptomoles) could be detected. This level of detection is approximately 3 orders of magnitude more sensitive than standard immunoassays for PSA. The antibody used as the conjugate in this example was a rabbit anti-mouse IgG polyclonal antibody; this reagent can serve as a "universal" conjugate to detect any mouse monoclonal antibody with high sensitivity.

E. Example 5

This example demonstrates the use of immunoRCA in a sandwich format on microarrays of polyclonal goat anti-human IgE antibody spotted onto glass slides using a pin-tool type microarraying robot. In these microarrays, approximately 0.5 nl of antibody solution was deposited in each spot, spots had a diameter of approximately 200 $\mu$m, and the spot-to-spot spacing was 250 $\mu$m. The anti-IgE microarrays were incubated with human IgE, and bound antigen was detected with a biotinylated anti-human IgE antibody and an anti-biotin monoclonal antibody that had been conjugated to an oligonucleotide containing an RCA-priming sequence.

Preparation of microarrays. Glass slides functionalized with thiol-silane were prepared as described above. Thiol-derivatized slides were activated by immersing in a solution of 0.5 mg/ml sulfo-GMBS (Pierce), 1% dimethylformamide, 99% ethanol for 1 hour at room temperature. Slides were rinsed with ethanol, dried under nitrogen, and stored in a vacuum dessicator until use. A solution of polyclonal goat anti-human IgE (BioSpacifics 0.5 mg/ml) was spotted onto the slides using a pin-tool type microarrayer (GeneMachines). Arrays were blocked with 2% BSA (Protease free), air-dried, and stored under nitrogen at 4° C. until use.

Antigen capture. Each microarray was blocked by adding a 50 $\mu$l volume of a 2 mg/ml BSA solution in 50 mM glycine (pH 9.0) and incubating for 1 hour at 37° C. in a humidity chamber. After blocking, slides were twice washed by immersion of the slides into a coplin jar containing 1×PBS/0.05% Tween 20 and allowing the slides to stand in wash for 2 min. followed by a 1 min. 1×PBS wash. A 10 $\mu$l volume of human serum was immediately added to each microarrays and incubated for 30 min. at 37° C. in a humidity chamber, and then washed with PBS/Tween 20 and PBS as described above.

ImmunoRCA. Goat anti-human IgE (BiosPacific, Inc.) was labeled with biotin using the BiotinTag Micro Biotinylation Kit (Sigma). 10 $\mu$l of the antibody at 2.5 ng/$\mu$l in PBS, 0.05% Tween 20, 1 mM EDTA was applied to each array and incubated at 37° C. for 30 minutes in a humid chamber. Slides were washed twice for two minutes in PBS, 0.05% Tween 20. A mouse monoclonal anti-biotin antibody conjugated to primer 1 was annealed with 50 nM Circle 1 in PBS, 0.05% Tween 20, 1 mM EDTA at 37° C. for 30 minutes. 10 $\mu$l was applied to each array and incubated at 37° C. for 30 minutes in a humid chamber, and then slides were washed twice. A 20 $\mu$l volume of reaction solution containing T7 native DNA polymerase (0.01 units/$\mu$l), 1 mM dNTPs, 0.04 mg/ml of SSB, 20 mM Tris HCl (pH 7.4), 10 mM MgCl$_2$ and 25 mM NaCl was then added to each microarray. The slides were incubated at 37° C. for 45 min, and the reaction was stopped by washing the slides in a 2×SSC/0.05% Tween 20 solution at room temperature. A 20 $\mu$l solution of 0.5 $\mu$M DNA decorators was added to each array and allowed to hybridize to the RCA product for 30 min. at 37° C. Slides were washed in 2×SSC at room temperature and spin-dried. Slides were scanned in a General Scanning Luminomics 5000 microarray scanner, and fluorescence was quantitated using QuantArray software.

Figure 9:
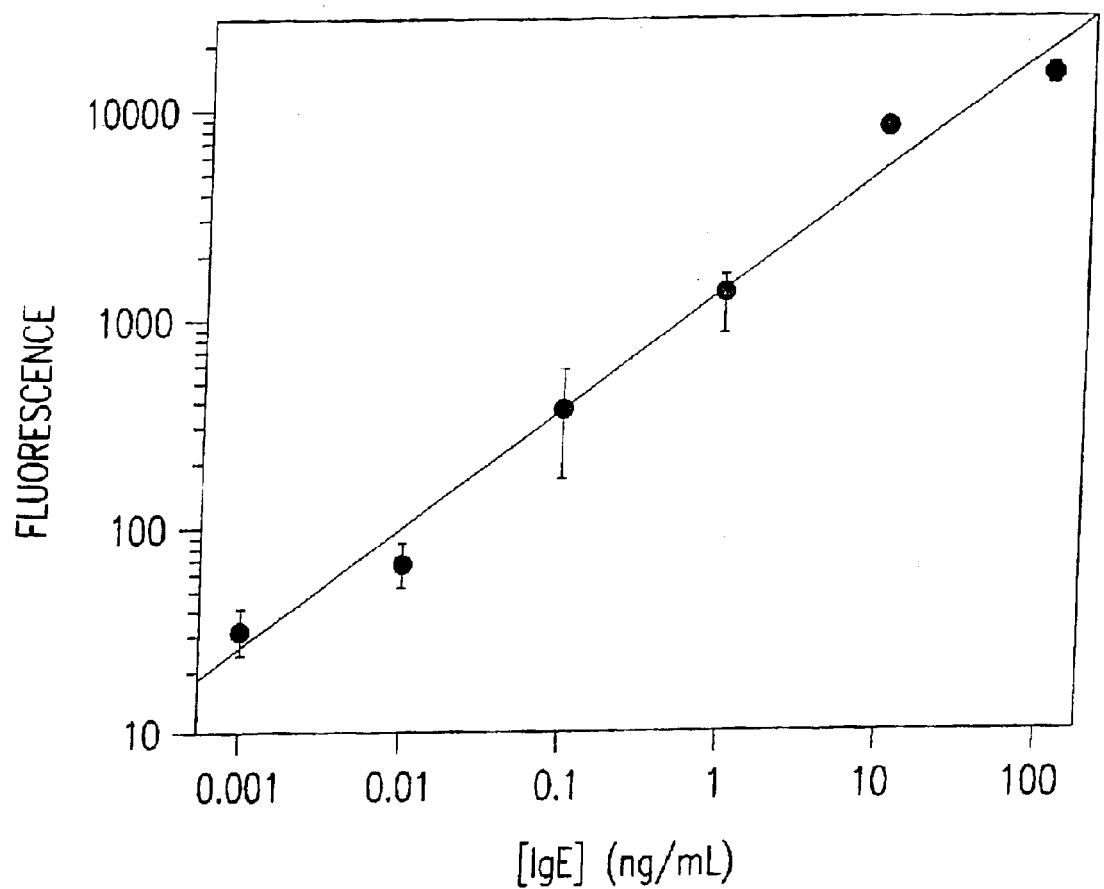
FIG. 9 is a graph of fluorescence versus IgE concentration (in ng/ml). The graph shows detection of IgE by immunoRCA in a microarray assay as described in Example 5. ImmunoRCA anti-human IgE microarray dose-response for purified IgE. Signals from 6 microarray spots were averaged for each point, and the background (no IgE) signal was subtracted.

The results (FIG. 9) indicate that immunoRCA has high sensitivity (down to 1 pg/mL), a wide dynamic range (5 logs), and excellent spot-to-spot reproducibility. Recently, a microarray-based immunoassay was reported that used alkaline phosphatase conjugates and the fluorescent substrate ELF for detection (Mendoza, et al., Biotechniques 27: 778–788 (1999)). The ELF-based assay required a specially constructed CCD-based camera to read the signal, and a sensitivity of approximately 10 ng/ml was achieved. In another report, antibodies labeled with a near-infrared dye were used to detect IgG subclasses on a microarray (Silzel, et al., Clin. Chem. 44: 2036–2043 (1998)); this system also required a specially designed imaging system and achieved a detection limit of approximately 15 ng/ml. In contrast, signal amplification by immunoRCA gives sensitivity in the pg/ml range and allows the assay results to be read with commonly available microarray scanners. ImmunoRCA can also be used to detect allergen-specific IgEs on microarrays with excellent clinical sensitivity and specificity. The antibody used as the conjugate for this was a monoclonal anti-biotin antibody. This reagent can be used to detect any biotinylated polyclonal or monoclonal antibody, as well as any other protein, nucleic acid or small molecule that can be biotinylated.

F. Example 6

This example demonstrates the detection of two proteins simultaneously in a single-molecule-counting mode of the disclosed method.

Preparation of capture slides. Slides were coated with 4-aminobutyl-dimethylmethoxysilane and derivatized with 1,4-phenylene-diisothiocyanate. A mixture of an avidin capture reagent, the oligonucleotide 5'-NH$_2$-GG$_{18}$G-biotin-3', and an anti-digoxigenin IgG capture reagent, digoxigenin-succinyl-$\epsilon$-aminocaproic acid hydride, each at a concentration of 5 $\mu$M, were spotted onto the activated slide surface in an array format (8–10 spots/array). Chemical coupling was allowed to proceed for 2 hours. The slides were rinsed twice in 0.5 mM glycine, pH 9.5 and then placed in the glycine solution for 30 min at 37° C. to block unreacted functional groups. The slides were incubated further in 50 mM glycine (ph 9.5), 0.15 M NaCl, 3% bovine serum albumin, 0.1% sonicated herring sperm DNA, 0.2% NaN$_3$ at 37° C. for 1 hour and washed in PBS, 0.1% Tween 20 for 3 min. at room temperature. The slides were then dried and stored at 4° C. until used.

Binding of antigens to capture slides. Various concentrations of avidin and sheep antidigoxigenin IgG, either singly or in defined molar ratios, were spiked into normal human serum. The spiked serum (1.0 $\mu$l) was applied to the capture arrays and the slides incubated in a moist chamber at 37° C. for 30 min. The slides then were washed twice in PBS/Tween20 and air-dried. Five $\mu$l of a mixture of 7.5 nM rabbit anti-avidin-Primer-1 conjugate and 7.5 nM rabbit anti-sheep IgG antibody-Primer-2 conjugate was applied to each array spot and incubated at 37° C. for up to 2.5 hours. The slides were washed eight times (1 min. each) and air-dried. Five µl of 0.2 µM solution of the two circular probes (circle 1 and circle 2) in 2×SSC, 0.1% Tween 20, 3% BSA, 0.1% sonicated herring sperm DNA was applied to each spot. After hybridization at 37° C. for 20 min., the slides were washed with 2×SSC, 0.1% Tween-20) at 37° C. for 5 min. and air-dried.

Figure 10:
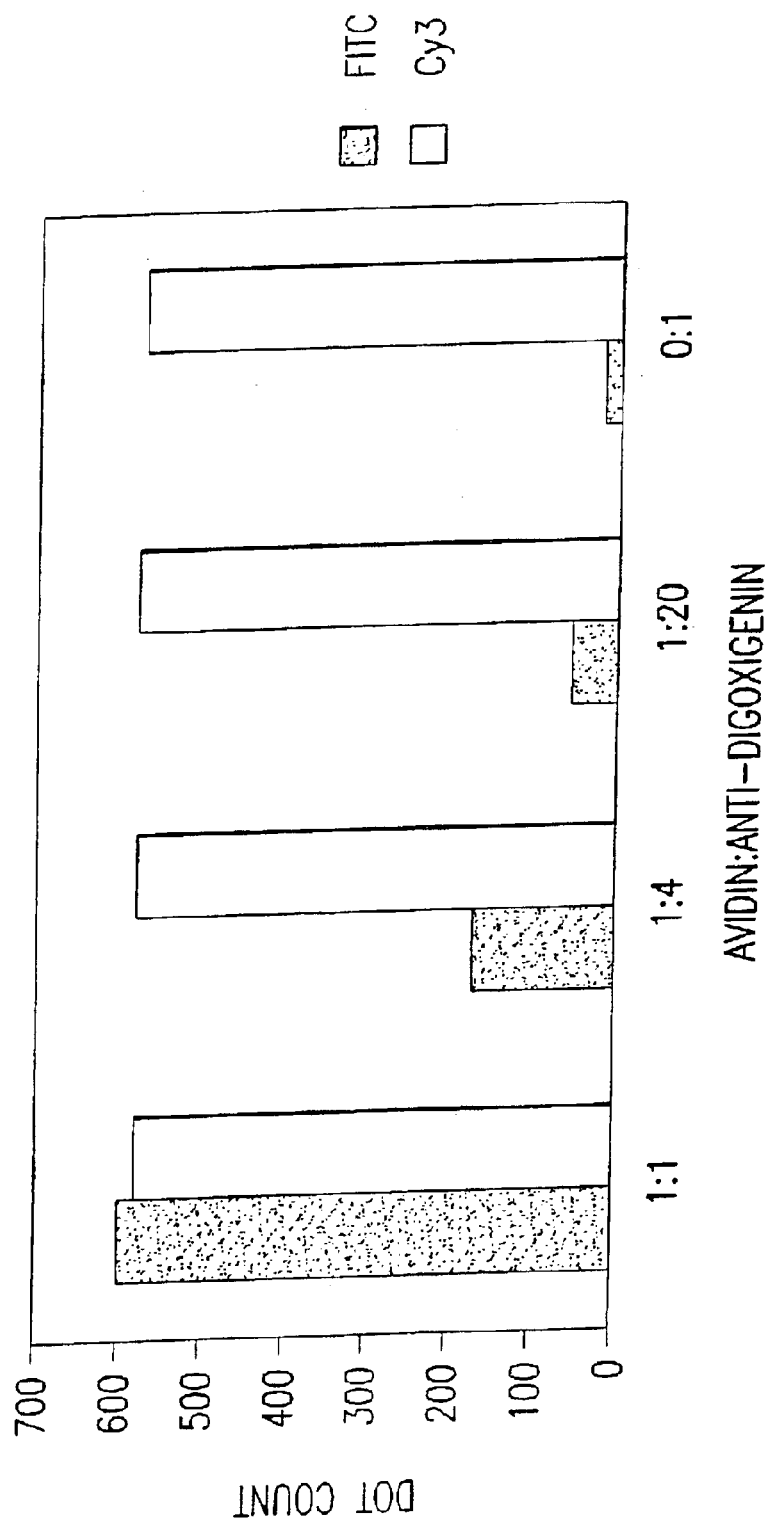
FIG. 10 is a bar graph of dot counts versus avidin:antidigoxigenin ratio. The graph shows dual antigen detection using immunoRCA-CACHET described in Example 6. The RCA products from the anti-avidin and the anti-sheep antibody conjugates were decorated with fluorescein- and Cy3-labeled detector oligonucleotides, respectively. The fluorescent signals were acquired separately using filter sets optimized for fluorescein and Cy3 detection.

RCA-CACHET Reactions. Five µl of RCA reaction mixture (50 mM NaCl, 50 mM Tris-HCl (pH 7.2), 5 mM MgCl$_2$, 0.5 mM of each dNTP, 1 mM DTT, SSB and 0.5 units/µl Sequenase) was applied to each spot and the slides were incubated at 37° C. for 15 min. After the slides were washed, they were air-dried and 5 µl of a solution containing 0.2 µM of double labeled (fluor+2,4 DNP) detector probes were applied to each array. Slides were incubated in the moist chamber for 30 min. at 37° C., then washed 5 times and air-dried. In order to collapse the RCA products into point sources of fluorescence so that single antigen-antibody complexes could be enumerated, five µl of 33 nM sheep anti-DNP IgM in PBS was added to each array spot, slides incubated at 37° C. for 45 min., washed for 3 min. in 2×SSC at room temperature and then air dried. Prolong antifade solution (Molecular Probes) was applied to the slide and the slide covered with a 20×20 mm coverslip. Separate FITC and Cy3 fluorophore microscope images were captured using a 63× objective lens and individual RCA products in each field counted manually. The FITC and Cy3 image were merged electronically and RNA signals pseudo-colored green and red. The discrete fluorescence signals had either a pure fluorescein or pure Cy3 spectra, the absence of signals with mixed spectra (yellow) indicated that each dot was generated by a single antibody-antigen complex. Quantitation of the avidin (light grey) and sheep anti-digoxigenin IgG (dark grey) signals demonstrated that the ratio of light/dark signals closely corresponded to the known input ratios of the two protein antigens (FIG. 10), further suggesting a 1-to-1 correspondence between antibody-antigen complexes and signals.

This example demonstrates that ImmunoRCA is ideally suited for microarray applications. During the entire isothermal RCA reaction, the resulting amplified DNA molecule remains covalently attached to the antibody-antigen complex. On microarrays, this process results in an approximately 3 log increase in detectable fluorescent signal over non-amplified signal detection approaches. A distinctive feature of RCA is the ability to precisely localize signals arising from a single DNA reporter molecule, thus enabling the visualization of individual recognition events on a solid surface. When the long single-stranded DNA product of RCA is decorated by hybridization to many complementary oligonucleotides labeled with both a reporter fluorophore and a hapten, such as 2,4-dinitrophenol, all of the fluorophores can be collapsed into a point source of light. When the number of molecular signals is extremely high, the signal from a spot on a microarray can be read using aggregate fluorescence. When the number of surface-bound antigens is smaller, however, the signals can be scored as discrete single molecule counts, and subattomoles of analyte can be visualized. ImmunoRCA carried out on microarrays thus provides assays with an extremely wide dynamic range; combining single molecule counting and total fluorescence output indicates a dynamic range between 6 and 7 logs.

G. Example 7

This example demonstrates the measurement of relative concentrations of a model protein (IgE) in two samples.

Figure 12:
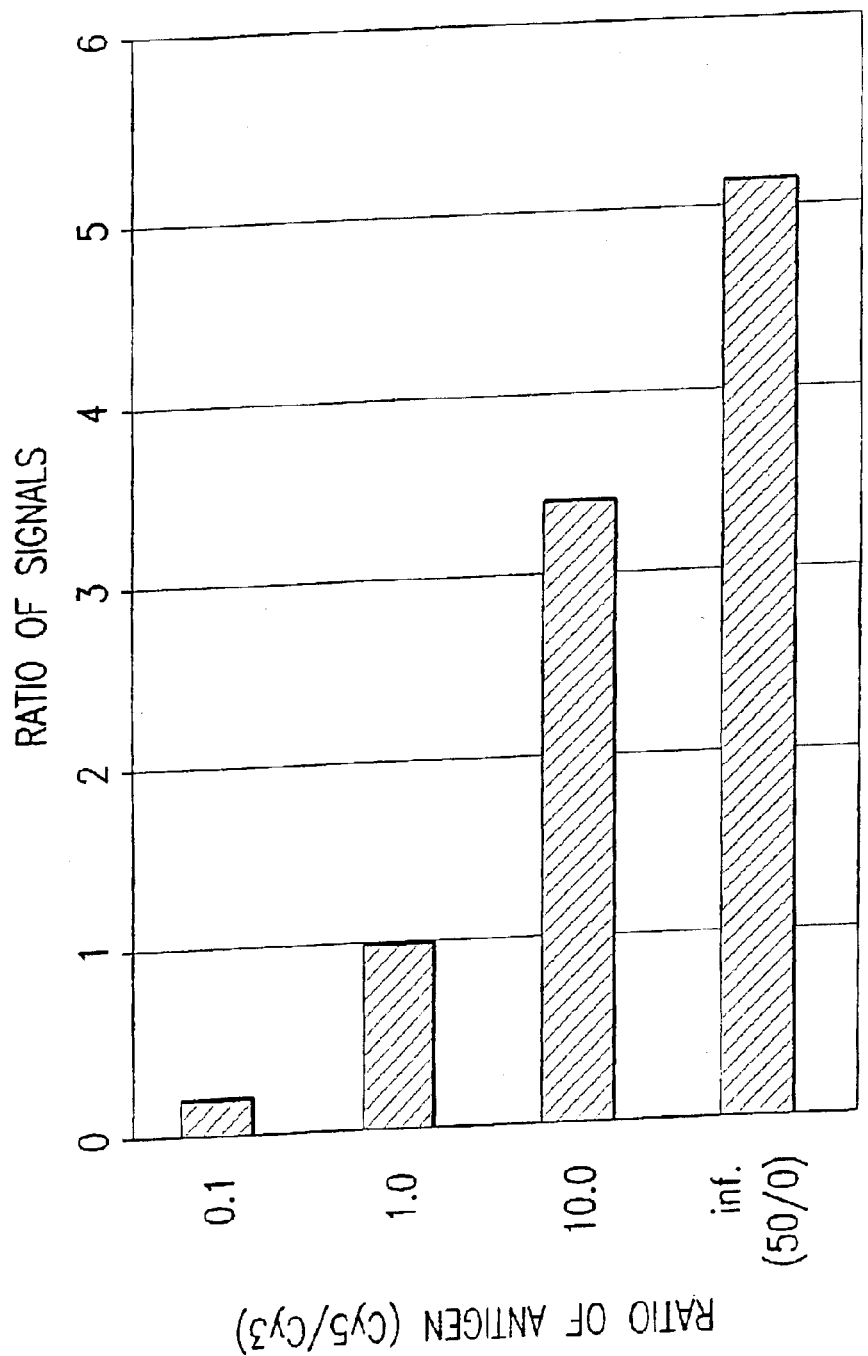
FIG. 12 is a bar graph of the ratio of Cy5 fluorescence intensity to Cy3 fluorescence intensity versus the ratio of IgE in two different samples. The graph shows expression profiling of the same analyte in two different samples as described in Example 7. A fixed concentration of IgE was incubated with one preparation of an anti-IgE antibody, and varying concentrations of IgE were incubated with a second preparation of an anti-IgE antibody. The two mixtures were simultaneously applied to a microarray consisting of anti-IgE capture antibodies. The amount of each IgE-anti-IgE complex was determined using immunoRCA with antibody-DNA conjugates against each complex containing two different rolling circle replication primers, and simultaneously detecting the resulting two TS-DNAs with Cy5-labeled and Cy3-labeled detector probes.
Figure 13:
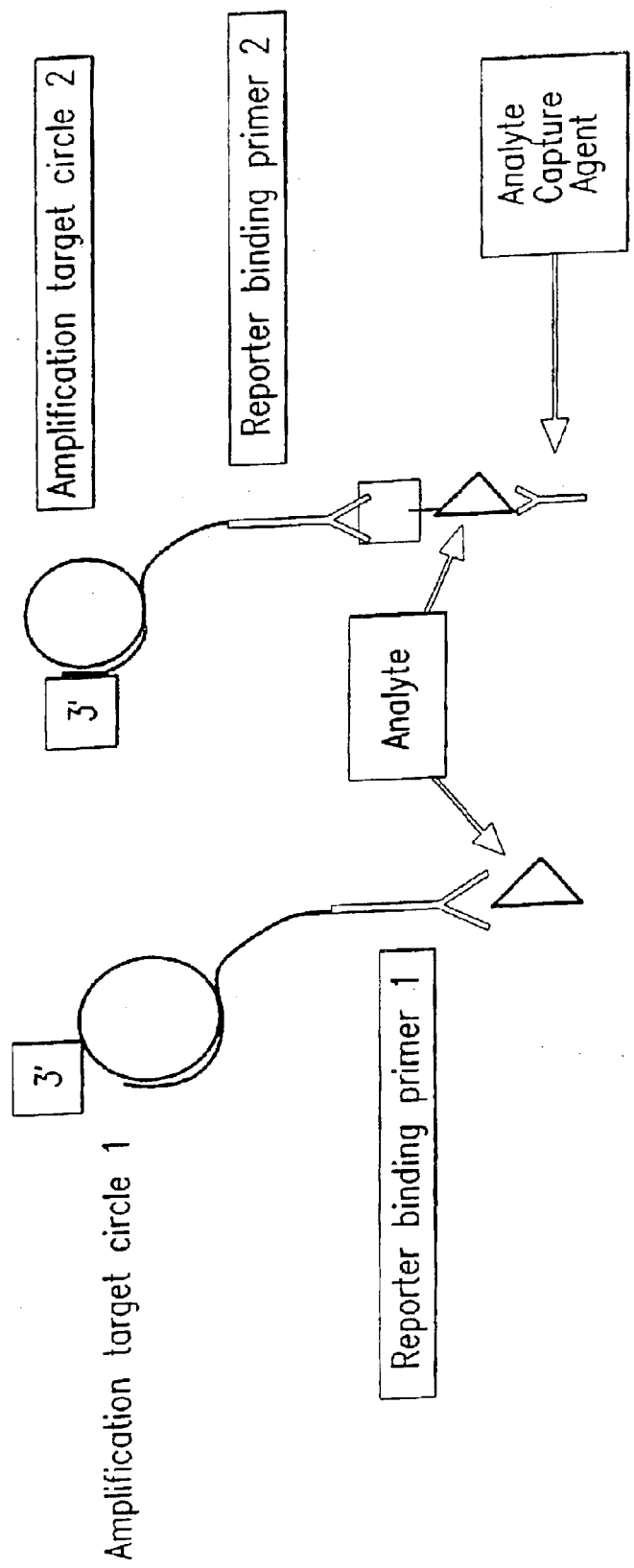
FIG. 13 is a diagram of an example of the disclosed method where the presence of two different forms of the same analyte are detected. This is accomplished by using two different reporter binding primers (reporter binding primers 1 and 2), each with a different specific binding molecule that binds to a different form of the analyte (in this case, phosphorylated and unphosphorylated forms of the analyte). Each different reporter binding primer has a different rolling circle replication primer and thus each primer mediates rolling circle amplification of a different amplification target circle (amplification target circles 1 and 2).

For two-color expression level profiling of IgE via linear RCA, microarrays were printed with polyclonal goat anti-human IgE (0.5 mg/ml, BiosPacific) capture antibody on glass slides activated by thiolsilanization plus treatment with GMBS. Two conjugates of MAb Anti-IgE (BiosPacific, clone# A37020047P) were constructed. For the first conjugate, the antibody was activated with sulfo-GMBS, then reacted with 5'thiol Pr2 (GTA CCA TCA TAT ATG TCC GTG CTA GAA GGA AAC AGT TAC A; SEQ ID NO:6). For the second conjugate, the antibody was biotinylated with EZ-link sulfo NHS-LC-Biotin (Pierce Chemical Co.). A conjugate of MAb Anti-biotin (Jackson Immunochemicals) was also constructed, by activating the antibody with sulfo-GMBS, then reacting with 5'thiol Pr1 (AAA AAA AAA AAA AAA CAC AGC TGA GGA TAG GAC AT; SEQ ID NO:7). Antibody-antigen complexes were pre-formed in separate reactions by incubating biotin~MAb Anti-IgE with 50 ng/ml IgE in one tube and Pr2~MAb Anti-IgE with 500, 50, 5, and 0 ng/ml IgE in a second tube for 1 hr at room temperature. Appropriate antibody-antigen complexes were then mixed, and 20 µl mixture applied per array. Capture of pre-formed complexes was carried out for 30 minutes at 37° C. Ten µl of a mixture containing 200 nM circle 1, 200 nM circle 2, and 2.5 ng/µl Pr1~Anti-biotin conjugate was then applied to each array and incubated at 37° C. for 30 minutes. The slides were then washed 2×2' in 1×PBS/0.05% Tween 20. Ten µl of linear RCA reaction mix (20 mM Tris-Cl, 10 mM MgCl$_2$, 25 mM NaCl, 1 mM each dNTP, 0.5 µM Cy5-labeled detector probes for circle 1 and Cy3-labeled detector probes for circle 2, 29.1 ng/µl E. coli SSB (Promega), 0.01U/µl T7 Native DNA Polymerase (USB), and 8% DMSO) was then applied to each array and incubated at 37° C. for 45 minutes. The slides were then washed in 1×PBS/0.05% Tween 20 and in 1×PBS, air-dried and scanned. As shown in FIG. 12, the ratio of Cy5 fluorescence intensity to Cy3 fluorescence intensity reflects the ratios of IgE in the two samples.

Measurement of relative concentrations of a protein in two samples is further exemplified using prostate-specific antigen (PSA) as a model. Varying concentrations of PSA (Biospacifics) were incubated with 5 ng/ul of either biotin or FITC labeled monoclonal anti-PSA in PBS/0.05% Tween20 for 30 minutes at 37° C. The PSA/FITC-anti-PSA and PSA/biotinylated anti-PSA complexes were then mixed together, and 20 ul of the mixture were incubated on a microarray for 30 minutes at 37° C. Slides were washed twice for two minutes in PBS/0.05% Tween20. The slides were incubated with 2.5 ng/µl of anti-biotin~primer 1 conjugate, anti-FITC~primer 2 conjugate, or a mixture of the two reagents. Microarrays were prepared by immobilizing Goat polyclonal anti-PSA antibody (Biospacifics, 0.3 mg/ml) on GMBS-activated thiosilane glass slides and blocked as described. Monoclonal anti-PSA antibody (Biospacifics) was labeled with either FITC or biotin using antibody labeling kits (Sigma Chemical Co., St. Louis, Mich.).

Figure 17:
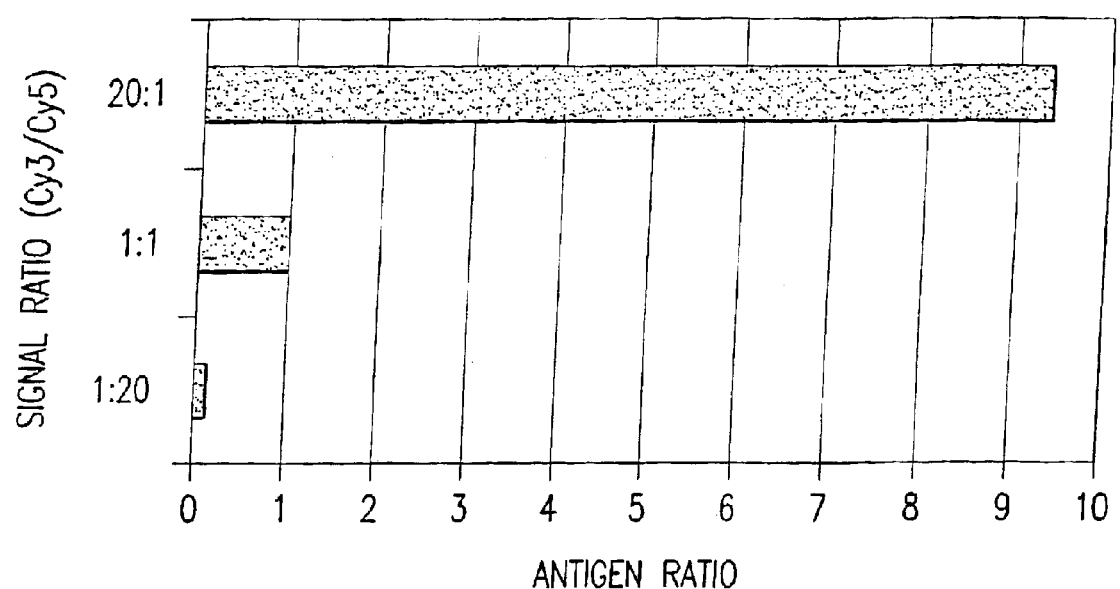
FIG. 17 is a bar graph of antigen ratio versus signal ratio from two-color detection of PSA from two different samples on a single microarray. The graph shows quantitation of PSA antigen by ImmunoRCA in two different samples, one with biotin-labeled anti-PSA and the other with FITC-labeled anti-PSA. The biotin and FITC samples were added to the same array and detected by immunoRCA using anti-biotin (primer 1) and anti-FITC (primer 2) conjugates. The ratio of Cy3 (primer 2) and Cy5 (primer 1) signal intensities is plotted as a function of the ratio of PSA antigen in the two samples as described in Example 7.

Linear RCA was performed on the microarrays with T7 Native DNA polymerase for 45 minutes at 37° C. in the presence of 50 nM each of Cy5-labeled Circle 1 and Cy3-labeled Circle 2 decorators. Slides were washed twice for two minutes in 2×SSC/0.05% Tween 20, rinsed for 1 minute in 1×SSC, dried, and scanned in a GSI Lumonics GSA5000 scanner at the appropriate settings for Cy3 and Cy5 fluorophores, respectively. As shown in FIG. 17, the ratio of Cy5 fluorescence intensity to Cy3 fluorescence intensity reflects the ratios of PSA in the two samples.

H. Example 8

This example describes methods and compositions for immobilizing analytes from complex biological samples and the use of the disclosed method for determining and quantitating their presence in the samples. The process is exemplified herein using samples containing allergens.

Allergen microarrays. Clean glass slides were derivatized with thiol as described in Example 4. Extracts of cat hair, dog hair, house dust mite (*D. farinae* and *D. pteronyssinus*), and peanut (ALK-Abello) were fractionated over PD-10 columns (Pharmacia) and then concentrated by ultrafiltration on Centricon YM-3 filters (Millipore). Spotting of the extracts onto the activated slides was accomplished using a pin-tool type microarrayer (GeneMachines). Human IgE and a 5'-amino modified RCA primer were spotted as positive controls. Arrays were blocked with 2% BSA (Protease free), air-dried, and stored under nitrogen at 4° C. until use.

ImmunoRCA. Each microarray was blocked by adding a 50 μL volume of a 2 mg/ml BSA solution in 50 mM glycine (pH 9.0) and incubating for 1 hour at 37° C. in a humidity chamber. After blocking, slides were washed twice with PBS, 0.05% Tween 20 for 2 minutes followed by a 1-min. wash in PBS. 10 μL of human serum was immediately added to each array, incubated for 30 minutes at 37° C. in a humidity chamber, and washed twice in PBS, 0.05% Tween 20. A mouse monoclonal anti-IgE antibody DNA conjugate was annealed with 50 nM circular DNA (sequence: 5'-TAG CAC GGA CAT ATA TGA TGG TAC CGC AGT ATG AGT ATC TCC TAT CAC TAC TAA GTG GAA GAA ATG TAA CTG TTT CCT TC; SEQ ID NO:8) in PBS, 0.05% Tween 20, 1 mM EDTA at 37° C. for 30 minutes. 10 μl was applied to each array and incubated at 37° C. for 30 minutes in a humid chamber. Slides were washed twice for two minutes in PBS, 0.05% Tween 20. RCA reaction and detection were carried out as described in Example 5.

The immunoRCA microarray assay was performed in 16 microwell-glass slides each well separated by a Teflon mask. Microarrays of 100–400 μm spots were printed in each microwell; each of these wells was used to assay a different sample, or negative or positive controls. Multiwell slides were also printed with arrays of anti-IgE capture antibodies in 6 of the 16 wells. Semi-automation of the immunoRCA assays on allergen microarrays in this multiwell format was implemented on an inexpensive Beckman BioMek liquid handling robot.

I. Example 9

This example describes use of the disclosed method for the multiplexed analysis of more than one analytes in a sample, as applied to the specific case of detection of cytokines.

Microarrays were prepared in 10 well Erie slides with thiol-silane/GMBS chemistry as described in Example 5. Briefly, polyclonal antibodies recognizing 5 cytokines (anti-bNGF, anti-IL1b, anti-TNFa, anti-IL6 and anti-IL1a) (R&D Systems, Minneapolis, Minn.) were dissolved at 0.5 mg/ml in PBS and used for microarraying in multiwell slides. The microarrays were blocked and incubated at 37° C. for 30 min with a sample containing 20 ng/ml cytokine in PBS/0.5% Tween. The microarrays were washed and incubated with a solution containing 2.5 μg/ml biotinylated monoclonal antibody (R&D Systems). The spots were detected by RCA with α-biotin/primer 1 conjugate, as described.

As shown in FIG. 18, TNF and IL1a were simultaneously detectable on the micro array when antibodies for both the cytokines were present. The specificity of the signal is demonstrated by the appearance of only one cognate signal when only of the antibodies was added.

It is understood that the disclosed invention is not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to "the antibody" is a reference to one or more antibodies and equivalents thereof known to those skilled in the art, and so forth.

Unless defined otherwise, all technical and scientific terms used herein have the same meanings as commonly understood by one of skill in the art to which the disclosed invention belongs. Although any methods and materials similar or equivalent to those described herein can be used in the practice or testing of the present invention, the preferred methods, devices, and materials are as described. Publications cited herein and the material for which they are cited are specifically incorporated by reference. Nothing herein is to be construed as an admission that the invention is not entitled to antedate such disclosure by virtue of prior invention.

Those skilled in the art will recognize, or be able to ascertain using no more than routine experimentation, many equivalents to the specific embodiments of the invention described herein. Such equivalents are intended to be encompassed by the following claims.

We claim:

1. A method for detecting one or more analytes, the method comprising (a) bringing into contact one or more analyte samples and one or more arrays, wherein each array comprises a set of analyte capture agents, wherein each analyte capture agent is immobilized on a solid support in a different predefined region of the solid support, wherein each analyte capture agent interacts with an analyte directly or indirectly, (b) prior to, simultaneous with, or following step (a), bringing into contact at least one of the analyte samples and one or more reporter binding primers, wherein each reporter binding primer comprises a specific binding molecule and a rolling circle replication primer, wherein each specific binding molecule interacts with an analyte directly or indirectly, (c) simultaneous with, or following, either or both steps (a) and (b), incubating the analyte samples, the arrays, and the reporter binding primers under conditions that promote interaction of the specific binding molecules, analytes, and analyte capture agents, (d) prior to, simultaneous with, or following step (b), bringing into contact the reporter binding primers and one or more amplification target circles, wherein the amplification target circles each comprise a single-stranded, circular DNA molecule comprising a primer complement portion, wherein the primer complement portion is complementary to at least one of the rolling circle replication primers, and incubating the reporter binding primers and amplification target circles under conditions that promote hybridization between the amplification target circles and the rolling circle replication primers, (e) following step (d) arid prior to, simultaneous with, or following steps (a), (b), or (c), incubating the reporter binding primers and amplification target circles under conditions that promote replication of the amplification target circles, wherein replication of the amplification target circles results in the formation of tandem sequence DNA, wherein detection of tandem sequence DNA indicates the presence of the corresponding analytes.

2. The method of claim 1 wherein the distance between the different predefined regions of the solid support is fixed.

3. The method of claim 1 wherein the distance between at least two of the different predefined regions of the solid support is variable.

4. The method of claim 1 wherein the analyte capture agents are immobilized to the solid support at a density exceeding 400 different analyte capture agents per cubic centimeter.

5. The method of claim 1 wherein the analyte capture agents are peptides.

6. The method of claim 1, wherein at least one array comprises at least 1,000 different analyte capture agents immobilized on the solid support.

7. The method of claim 1, wherein at least one array comprises at least 10,000 different analyte capture agents immobilized on the solid support.

8. The method of claim 1, wherein at least one array comprises at least 100,000 different analyte capture agents immobilized on the solid support.

9. The method of claim 1, wherein at least one array comprises at least 1,000,000 different analyte capture agents immobilized on the solid support.

10. The method of claim 1, wherein each of the different predefined regions is physically separated from each other of tile different regions.

11. The method of claim 1, wherein the solid support comprises at least one thin film, membrane, bottles, dishes, fibers, woven fibers, shaped polymers, particles, beads, microparticles, or a combination.

12. The method of claim 1, wherein the solid support comprises acrylamide, agarose, cellulose, nitrocellulose, glass, polystyrene, polyethylene vinyl acetate, polypropylene, polymethacrylate, polyethylene, polyethylene oxide, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, or polyamino acids.

13. The method of claim 1 wherein the solid support is porous.

14. The method of claim 1, wherein the analyte capture agents in the different predefined regions are at least 20% pure.

15. The method of claim 1, wherein the analyte capture agents in the different predefined regions are at least 50% pure.

16. The method of claim 1, wherein the analyte capture agents in the different predefined regions are at least 80% pure.

17. The method of claim 1, wherein the analyte capture agents in the different predefined regions are at least 90% pure.

18. The method of claim 11 wherein the solid support comprises at least two thin films, membranes, bottles, dishes, fibers, woven fibers, shaped polymers, particles, beads, microparticles, or a combination.

19. The method of claim 1 wherein the location of tandem sequence DNA on the solid support indicates the presence in the analyte sample of the analyte corresponding to the analyte capture agent at that location of the solid support.

20. The method of claim 1 further comprising bringing into contact at least one of the analyte samples and at least one of the reporter binding primers with at least one accessory molecule, wherein the accessory molecule affects the interaction of at least one of the analytes and at least one of the specific binding molecules or at least one of the analyte capture agents.

21. The method of claim 20 wherein the accessory molecule is brought into contact with at least one of the analyte samples, at least one of the reporter binding primers, or both, prior to, simultaneous with, or following step (b).

22. The method of claim 20 wherein the accessory molecule is associated with the solid support.

23. The method of claim 22 wherein the accessory molecule is associated with the solid support by bringing the accessory molecule into contact with the solid support prior to, simultaneous with, or following step (a).

24. The method of claim 20 wherein the accessory molecule is a protein kinase, a protein phosphatase, an enzyme, or a compound.

25. The method of claim 20 wherein the accessory molecule is a molecule of interest, wherein one or more of the analytes are test molecules, wherein interactions of the test molecules with the molecule of interest are detected.

26. The method of claim 20 wherein at least one of the analytes is a molecule of interest, wherein the accessory molecule is a test molecule, wherein interactions of the test molecule with the molecule of interest are detected.

27. The method of claim 1 wherein the analyte samples include one or more first analyte samples and one or note second analyte samples, wherein the reporter binding primers include one or more firs reporter binding primers and one or more second reporter binding primers, the method further comprising, following step (b) and prior to step (a), mixing one or more of the first analyte samples and one or more of the second analyte samples, wherein for each first reporter binding primer there is a matching second reporter binding primer, wherein the specific binding molecules of the first reporter binding primers interacts with the same analyte as the specific binding molecules of the matching second reporter binding primer, wherein the rolling circle replication primer of each different reporter binding primer is different, wherein each different rolling circle replication primer primes replication of a different one of the amplification target circles, wherein each different amplification target circle produces a different tandem sequence DNA, wherein the presence or absence of the same analyte in different analyte samples is indicated by the presence or absence of corresponding tandem sequence DNA.

28. The method of claim 27 wherein the tandem sequence DNA corresponding to one of the analytes and produced in association with a first reporter binding primer is in the same location on the solid support as tandem sequence DNA corresponding to the same analyte and produced in association with the matching second reporter binding primer, wherein the presence or absence of the same analyte in different analyte samples is indicated by the presence or absence of corresponding tandem sequence DNA.

29. A method for detecting one or more analytes, the method comprising (a) bringing into contact one or more analyte samples and one or more reporter binding primers, wherein each reporter binding primer comprises a specific binding molecule and a rolling circle replication primer, wherein each specific binding molecule interacts with an analyte directly or indirectly, and incubating the analyte samples arid the reporter binding primers under conditions that promote interaction of the specific binding molecules and analytes, (b) prior to, simultaneous with, or following step (a), bringing into contact one or more first analyte capture agents and one or more first analyte samples, and bringing into contact one or more second analyte capture agents and one or more second analyte samples, wherein each analyte capture agent comprises an analyte interaction portion and a capture portion, wherein for each first analyte capture agent there is a matching second analyte capture agent, wherein the analyte interaction portions of the first analyte capture agents interact with the same analyte as the analyte interaction portions of the matching second analyte capture agents, wherein the capture portions of the first and second analyte capture agents each interact with a specific binding molecule of one or more or the reporter binding primers, wherein the capture portions of the first analyte capture agents interact with different specific binding molecules than the capture portions of the matching second analyte capture agents, (c) prior to, simultaneous with, or following step (a), bringing into contact the reporter binding primers and one or more amplification target circles, wherein the amplification target circles each comprise a single-stranded, circular DNA molecule comprising a primer complement portion, wherein the primer complement portion is complementary to at least one of the rolling circle replication primers, and incubating the reporter binding primers and amplification target circles under conditions that promote hybridization between the amplification target circles and the rolling circle replication primers, (d) following step (c) and prior to, simultaneous with, or following step (a), incubating the reporter binding primers and amplification target circles under conditions that promote replication of the amplification target circles, wherein replication of the amplification target circles results in the formation of tandem sequence DNA, wherein each different specific binding molecule is part of a different one of the reporter binding primers, wherein the rolling circle replication primer of each different reporter binding primer is different, wherein each different rolling circle replication primer primes replication of a different one of the amplification target circles, wherein each different amplification target circle produces a different tandem sequence DNA, wherein the presence or absence of the same analyte in different analyte samples is indicated by the presence or absence of corresponding tandem sequence DNA.

30. The method of claim 29 further comprising mixing one or more of the first analyte samples and one or more of the second analyte samples.

31. The method of claim 29 further comprising mixing the one or more first analyte capture agents and the one or more second analyte capture agents.

32. The method of claim 31 wherein mixing the one or more first analyte capture agents and the one or more second analyte capture agents is accomplished by associating, simultaneously or sequentially, the one or more first analyte capture agents and the one or more second analyte capture agents with the same solid support.

33. The method of claim 29 wherein the tandem sequence DNA corresponding to one of the analytes and produced in association with a first analyte capture agent is in the same location as, and is simultaneously detected with, tandem sequence DNA corresponding to the same analyte and produced in association with the matching second analyte capture agent, wherein the presence or absence of the same analyte in different analyte samples is indicated by the presence or absence of corresponding tandem sequence DNA.

34. The method of claim 29 wherein the capture portion of each first analyte capture agent is the same, wherein the reporter binding primers corresponding to the first analyte capture agents are the same, wherein the amplification target circles corresponding to the first analyte capture agents are the same, wherein the capture portion of each second analyte capture agent is the same, wherein the reporter binding primers corresponding to the second analyte capture agents are the same, wherein the amplification target circles corresponding to the second analyte capture agents are the same.

35. A method for detecting one or more analytes, the method comprising (a) treating one or more analyte samples so that one or more analytes are modified, (b) bringing into contact at least one of the analyte samples and one or more reporter binding primers, wherein each reporter binding primer comprises a specific binding molecule and a rolling circle replication primer, wherein each specific binding molecule interacts with a modified analyte directly or indirectly, and incubating the analyte samples and the reporter binding primers under conditions that promote interaction of the specific binding molecules and modified analytes, (c) prior to, simultaneous with, or following steps (a) or (b), bringing into contact the reporter binding primers and one or more amplification target circles, wherein the amplification target circles each comprise a single-stranded, circular DNA molecule comprising a primer complement portion, wherein the primer complement portion is complementary to at least one of the rolling circle replication primers, and incubating the reporter binding primers and amplification target circles under conditions that promote hybridization between the amplification target circles and the rolling circle replication primers, (d) following step (c) and prior to, simultaneous with, or following steps (a) or (b), incubating the reporter binding primers and amplification target circles under conditions that promote replication of the amplification target circles, wherein replication of the amplification target circles results in the formation of tandem sequence DNA, wherein detection of tandem sequence DNA indicates the presence of the corresponding analytes.

36. The method of claim 35 wherein all of the analytes are modified by associating a modifying group to the analytes, wherein the modifying group is the same for all of the analytes, wherein all of the specific binding molecules interact with the modifying group.

* * * * *

UNITED STATES PATENT AND TRADEMARK OFFICE
CERTIFICATE OF CORRECTION

PATENT NO. : 6,921,642 B2
DATED : July 26, 2005
INVENTOR(S) : Kingsmore et al.

It is certified that error appears in the above-identified patent and that said Letters Patent is hereby corrected as shown below:

Title page,
Item [73], Assignee, change from "QLAGEN GmbH (DE)" to read
-- QIAGEN GmbH (DE) --.

Signed and Sealed this

Twenty-seventh Day of September, 2005

JON W. DUDAS
*Director of the United States Patent and Trademark Office*